US009346858B2

(12) United States Patent
Ko et al.

(10) Patent No.: US 9,346,858 B2
(45) Date of Patent: May 24, 2016

(54) **PROTEINS WITH REPETITIVE BACTERIAL-IG-LIKE (BIG) DOMAINS PRESENT IN *LEPTOSPIRA* SPECIES**

(71) Applicants: The United States of America as represented by the Department of Veterans Affairs, Washington, DC (US); The Regents of the University of California, Oakland, CA (US); Cornell Research Foundation, Inc., Ithaca, NY (US); Fundação Oswaldo Cruz—FIOCRUZ, Rio de Janeiro (BR)

(72) Inventors: Albert I. Ko, Salvador (BR); Mitermayer Galvão Reis, Salvador (BR); Julio Henrique Rosa Croda, Salvador (BR); Isadora Cristina Siqueira, Salvador (BR); David A. Haake, Los Angeles, CA (US); James Matsunaga, Los Angeles, CA (US); Lee W. Riley, Berkeley, CA (US); Michele Barocchi, Los Angeles, CA (US); Tracy Ann Young, Berkeley, CA (US)

(73) Assignees: Cornell Research Foundation, Inc., Ithaca, NY (US); The Regents of the University of California, Oakland, CA (US); The United States of America as represented by the Department of Veterans Affairs, Washington, DC (US); Fundação Oswaldo Cruz—FIOCRUZ, Rio de Janeiro (BR)

( * ) Notice: Subject to any disclaimer, the term of this patent is extended or adjusted under 35 U.S.C. 154(b) by 0 days.

(21) Appl. No.: 14/819,045

(22) Filed: Aug. 5, 2015

(65) Prior Publication Data

US 2015/0329599 A1 Nov. 19, 2015

Related U.S. Application Data

(62) Division of application No. 14/281,580, filed on May 19, 2014, now Pat. No. 9,133,250, which is a division of application No. 13/869,660, filed on Apr. 24, 2013, now Pat. No. 8,802,835, which is a division of application No. 13/525,157, filed on Jun. 15, 2012, now Pat. No. 8,445,658, which is a division of application No. 13/359,354, filed on Jan. 26, 2012, now Pat. No. 8,216,594, which is a division of application No. 13/216,214, filed on Aug. 23, 2011, now Pat. No. 8,124,110, which is a division of application No. 13/078,879, filed on Apr. 1, 2011, now Pat. No. 8,021,673, which is a division of application No. 12/728,177, filed on Mar. 19, 2010, now Pat. No. 7,935,357, which is a division of application No. 11/332,464, filed on Jan. 17, 2006, now Pat. No. 7,718,183, which is a division of application No. 11/005,565, filed on Dec. 7, 2004, now abandoned, which is a division of application No. 10/147,299, filed on May 17, 2002, now abandoned.

(51) Int. Cl.

| | |
|---|---|
| ***C07H 21/04*** | (2006.01) |
| ***C07K 14/20*** | (2006.01) |
| ***C12Q 1/68*** | (2006.01) |

(52) U.S. Cl.

CPC ................ *C07K 14/20* (2013.01); *C07H 21/04* (2013.01); *C12Q 1/689* (2013.01)

(58) Field of Classification Search

None

See application file for complete search history.

(56) References Cited

PUBLICATIONS

Palaniappan et al (Infect. Immun. Nov. 2002 vol. 70 No. 11, pp. 5924-5930).*

Barocchi et al., "The Role of Bacterial Ig-like Protein in Leptospiral Pathogenesis: Biochemical analysis and localization studies by Immuno-Electron Microscopy," *2nd Meeting of the International Leptospirosis Society*, 2002. (Abstract; 1 page).

Chothia et al., "The relation between the divergence of sequence and structure in proteins," *The EMBO Journal*, 5(4): 823-826, 1986.

Croda et al., "Evaluation of a Putative *Leptospira* Virulence Factor, Bacterial Ig-like (Big) Protein, as a Serodiagnostic Marker for Leptospirosis," *2nd Meeting of the International Leptospirosis Society*, 2002. (Abstract; 1 page).

Croda et al., "Evaluation of recombinant Leptospira Bacterial Ig-like (Big) protein for leptospirosis serodiagnosis," *40th Annual Meeting of the Infections Disease Society of America*, 2002. (Abstract; 1 page).

Croda et al., "Leptospira Immunoglobulin-Like Proteins as Serodiagnostic Marker for Acute Leptospirosis," *J. Clin. Microbiol.*, 45(5): 1528-1534, 2007.

Greenspan et al., "Defining epitopes: It's not as easy as it seems," *Nature Biotechnology*, 7: 936-937, 1999.

Matsunaga et al., "Expression of a putative leptospiral lipoprotein containing immunoglobulin-like domains is correlated with virulence," *2nd Meeting of the International Leptospirosis Society*, 2002. (Abstract; 1 page).

Matsunaga et al., "Pathogenic Leptospira species express surface-exposed proteins belonging to the bacterial immunoglobulin superfamily," *Mol. Microbiol.*, 49(4): 929-945, 2003.

Mikayama et al., "Molecular cloning and functional expression of a cDNA encoding glycosylation-inhibiting factor," *Proc. Natl. Acad. Sci. USA*, vol. 90(21): 10056-10060, 1993.

Palaniappan et al., Submitted. Aug. 2002, GenBank Accession No. Q7X2A1.

Ren et al., Submitted. Mar. 2002, GenBank Accession No. Q8EZS3.

Rudinger et al., "Peptide Hormones," *Biol. Council*, pp. 5-7, 1976.

* cited by examiner

*Primary Examiner* — Jennifer Graser

(74) *Attorney, Agent, or Firm* — Klarquist Sparkman, LLP

(57) ABSTRACT

The invention relates to three isolated DNA molecules that encode for proteins, BigL1, BigL2 and BigL3, in the *Leptospira* sp bacterium which have repetitive Bacterial-Ig-like (Big) domains and their use in diagnostic, therapeutic and vaccine applications. According to the present invention, the isolated molecules encoding for BigL1, BigL2 and BigL3 proteins are used for the diagnosis and prevention of infection with *Leptospira* species that are capable of producing disease in humans and other mammals, including those of veterinary importance.

11 Claims, 13 Drawing Sheets

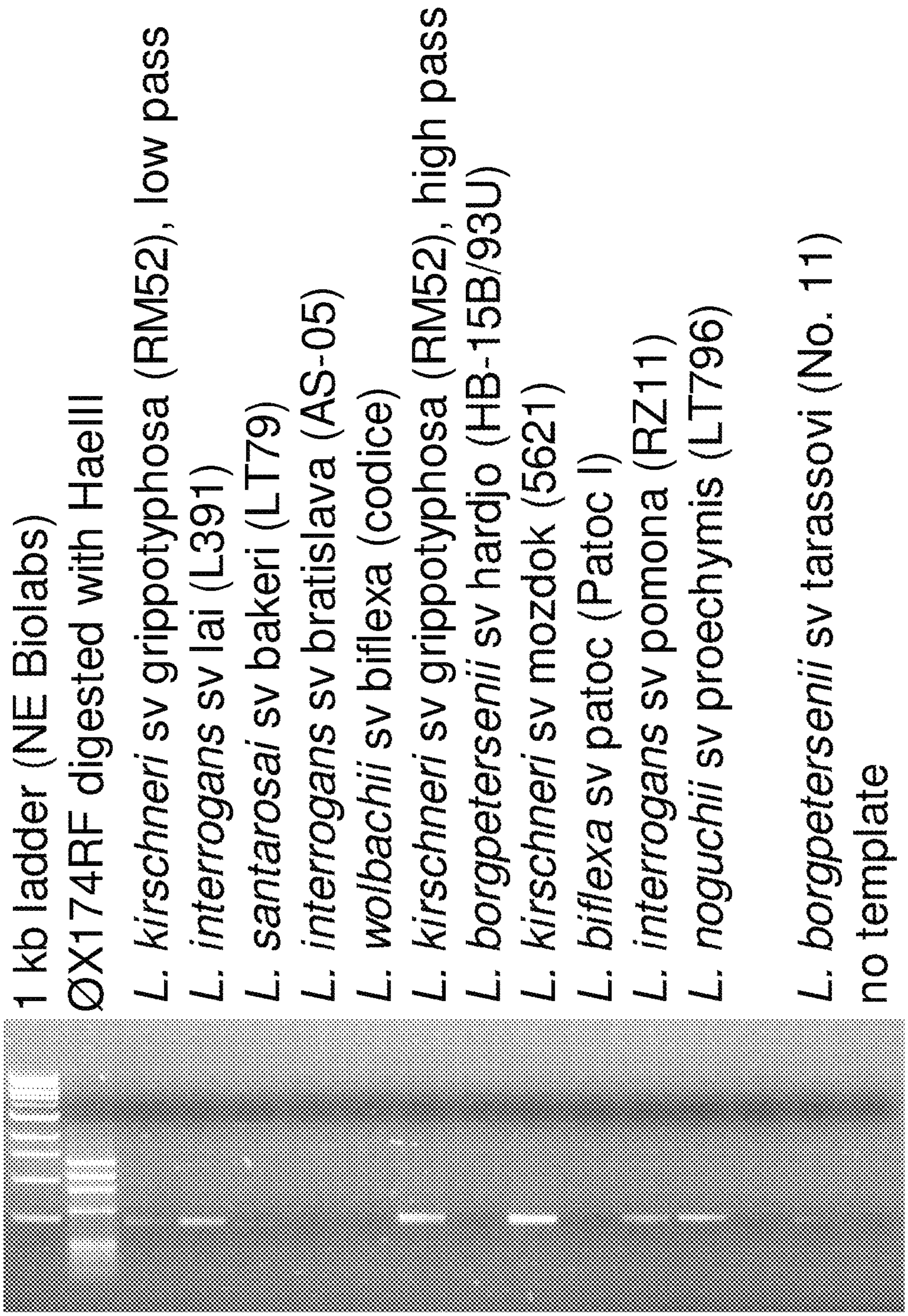

FIG. 3

1 kb ladder (NE Biolabs)
ØX174RF digested with HaeIII
L. kirschneri sv grippotyphosa (RM52), low pass
L. interrogans sv lai (L391)
L. santarosai sv bakeri (LT79)
L. interrogans sv bratislava (AS-05)
L. wolbachii sv biflexa (codice)
L. kirschneri sv grippotyphosa (RM52), high pass
L. borgpetersenii sv hardjo (HB-15B/93U)
L. kirschneri sv mozdok (5621)
L. biflexa sv patoc (Patoc I)
L. interrogans sv pomona (RZ11)
L. noguchii sv proechymis (LT796)
L. borgpetersenii sv tarassovi (No. 11)
no template IgM ELISA reactivity Serum Dilution

1:200

SEQUENCE LISTING

<160> NUMBER OF SEQ ID NOS: 30

<210> SEQ ID NO 1
<211> LENGTH: 3672
<212> TYPE: DNA
<213> ORGANISM: Leptospira kirschneri -continued

<400> SEQUENCE: 1

```
atgaagagaa cattttgtat ttcgattctt ctttcgatgt tttttcaaag ttgtatgtct     60
tggccacttt taaccagtct cgcgggttta gcagctggta aaaaaagtaa tgggctgccc    120
tttttccacc ttctattaag taactctgat ccagttatta caaggatcga gctcagttat    180
caaaattctt ccatcgcaaa aggtacaagt acaactctcg aagtcaccgc aatctttgat    240
aacggaacaa atcagaatat tacggattcg acatctatcg tttccgatgc ccaatcaatc    300
gttgacattc aaggtaacag agtcagagga atcgcttctg gttcttccat tataaaagct    360
gaatacaacg ggatgtattc tgaacaaaaa attacggtta caccagccac gataaactca    420
attcaagtta cgagtttaga tgacggtata ttacctaaag gtacaaatcg tcaatttgct    480
gccatcggta tcttttcgga tggttctcat caagatattt ccaacgatcc attgatcgtt    540
tggtcttcca gtaatataga tttagttcga gtagatgatt ccggtttggc ctcaggtatc    600
aatttaggaa cggctcatat tcgtgcatcc tttcaatcaa aacaagcctc cgaagagata    660
actgttggtg acgctgttct ttcttctatc caagtaactt ccaacagtcc aaatattcct    720
ctcggaaaaa aacaaaaact cacagctact ggaatttatt cggataactc taacagggat    780
atttcctctt ctgttatctg gaattcttct aattccacta tcgctaatat tcagaataac    840
ggaatattag aaacagctga tactggaatt gttactgttt ctgcttctag aggtaatata    900
aatggttcca taaaactaat cgtcactcct gctgccttag tttctatttc tgtttctcct    960
acaaattctg cagtagcaaa aggtttacaa gaaaacttta aagctacagg gatctttaca   1020
gataattcga actcagatat tacagatcaa gttacttggg attcttctaa tccggatatt   1080
ctttccattt ccaatgcaag tgatagccac gggttagctt ccacactcaa ccaaggaaat   1140
gttaaggtca ccgcttccat cggtggaata caaggatcca ctgattttaa agttacacaa   1200
gaggtattaa cttccatcga agtttctcca gttttacctt caattgcaaa aggactaact   1260
cagaaattta cggcgatcgg gatttttacg gataactcca aaaaagatat tacaaatcaa   1320
gtcacttgga attcttcttc agcaatcgca agcgtgtcta acttagatga taataaaggt   1380
ctgggaaaag ctcacgctgt tggagacacg actattaccg ctactttagg aaaagtttca   1440
ggtaaaactt ggtttactgt agttcctgcg gttctcactt ctattcaaat caatcctgta   1500
aatccttctc ttgcaaaagg gttaactcaa aaatttacgg ctactgggat ctactctgac   1560
aactctaaca aggacattac ttcctccgtt acttggttct catccgattc ttcaatcgca   1620
acaatttcaa acgccaaaaa aaatcaagga aactcttacg gagcagctac aggagcaacg   1680
gatattaaag ccacattcgg aaaggtaagt agtccagttt ctacgttatc cgttactgct   1740
gcaaaacttg ttgaaataca aatcacaccg gccgctgctt ccaaagcaaa gggaatttcc   1800
gaaagattta aagcaaccgg tatttttaca gacaactcta attccgatat tacaaatcag   1860
gtcacttgga gttcatctaa tacagatatt cttaccgttt ccaatacaaa cgccaaacgc   1920
gggttaggtt ccactttaaa acaaggaact gttaaagtta tcgcttccat gggtggaatc   1980
gaaagttctg tagattttac cgtcacacag gctaatttga cttcgatcga agtctctcca   2040
actcgctctt cgattgcaaa aggactaact caaaaattta ccgctatagg tatttttacg   2100
gatcattcta agaaggatat tacagagcaa gttacttgga agtcttcttc gaaagtatta   2160
aatatgttga atgcatccgg tgaagaagga agaggtaagg caatttcagt cgggaaagcg   2220
accattactg caaccttaga aaaactttcc gggaaagctg atattacagt tactcccgcg   2280
gttcttactt caattcaaat cagtcctgtg aaaccttctc ttgtaaaagg gttaacagaa   2340
```

```
aatttttctg ctacaggtat ctactctgat aattccagca aggacataac ttcctccgtt   2400

acatggcatt cgttcaacaa ctctgttgca acgatctcga acacgaaaaa ttaccatgga   2460

caagctcacg caaccggtac agggatagtg ggtattaaag cgacattggg aaatgtaagc   2520

agcccagttt ccaaattatc cgttaccgca gcagaactgg ttgagattgt gttaaatcct   2580

actttatctc acaaggccaa gggacttact gaaaatttta aagcgaccgg cgtatttacg   2640

gacaattcga caaaagatat taccgaccag gttacttgga aatcttccaa tactgcctac   2700

gcagaaattt caaacgcaac tggaagtaaa ggggttgtta atgcactctc gaagggaacg   2760

agtcacattt ccgctacctt aggttcaatt tcaagtgcaa atgcgacatt ccaagttact   2820

ccagcaaaaa tagcttcgat cgaaataaca ccaaataatt tcttcttgat caaaaaactt   2880

agttatccat ttaaagcaat tggaatctat acggataata caaagacaga cattacaaaa   2940

caagtttcct ggtcttcctc tgatccgaat gttgcatcga tcgataacac attttcattg   3000

gctggctcag ctaccgcaat cgatgatgga aaaacgaaca tcactgcaac gttatccgac   3060

tctatgtccg cttccactac tttgtatgtc acttctgcta cgcttgttga catagaagta   3120

aaacctagta tcttcgttct gagtgaaggt cttacactac aactgaccgc taccggcatc   3180

tattcggatt actctaccta tgatttgact caggttgtaa cgtggacttc cagcgaacca   3240

tccaacattt cgatcgaaaa tacagccggt aaaaaaggta aagtaacggc tcttgcattt   3300

ggagcttcag aatttacggc aacctacgat tctattgaaa gtaatcgagc ttggatattt   3360

gtcaatgacg agaaatttgt aaacataacc attagttctt ctcaagtttt gacagacaag   3420

ggcttgactc aacaattcaa agcaatcgga actttcgaaa aaggtagcga acttgacctt   3480

acggatcttg taacctggaa gtcctctgat tctaaggtag cttctatcgg taactctaat   3540

gatgacagag gtttaataac accgctttct gtaggttcct ctaaaatttc tgcgacttac   3600

aattctatcc atagtaactc tattgatttt gaagtaactc cagaaatatt agcctctatt   3660

aaaacgaagc cg                                                       3672
```

<210> SEQ ID NO 2
<211> LENGTH: 1224
<212> TYPE: PRT
<213> ORGANISM: Leptospira kirschneri

<400> SEQUENCE: 2

```
Met Lys Arg Thr Phe Cys Ile Ser Ile Leu Leu Ser Met Phe Phe Gln
1               5                   10                  15

Ser Cys Met Ser Trp Pro Leu Leu Thr Ser Leu Ala Gly Leu Ala Ala
            20                  25                  30

Gly Lys Lys Ser Asn Gly Leu Pro Phe Phe His Leu Leu Leu Ser Asn
        35                  40                  45

Ser Asp Pro Val Ile Thr Arg Ile Glu Leu Ser Tyr Gln Asn Ser Ser
    50                  55                  60

Ile Ala Lys Gly Thr Ser Thr Thr Leu Glu Val Thr Ala Ile Phe Asp
65                  70                  75                  80

Asn Gly Thr Asn Gln Asn Ile Thr Asp Ser Thr Ser Ile Val Ser Asp
                85                  90                  95

Ala Gln Ser Ile Val Asp Ile Gln Gly Asn Arg Val Arg Gly Ile Ala
            100                 105                 110

Ser Gly Ser Ser Ile Ile Lys Ala Glu Tyr Asn Gly Met Tyr Ser Glu
        115                 120                 125
```

-continued

```
Gln Lys Ile Thr Val Thr Pro Ala Thr Ile Asn Ser Ile Gln Val Thr
    130                 135                 140

Ser Leu Asp Asp Gly Ile Leu Pro Lys Gly Thr Asn Arg Gln Phe Ala
145                 150                 155                 160

Ala Ile Gly Ile Phe Ser Asp Gly Ser His Gln Asp Ile Ser Asn Asp
                165                 170                 175

Pro Leu Ile Val Trp Ser Ser Ser Asn Ile Asp Leu Val Arg Val Asp
            180                 185                 190

Asp Ser Gly Leu Ala Ser Gly Ile Asn Leu Gly Thr Ala His Ile Arg
        195                 200                 205

Ala Ser Phe Gln Ser Lys Gln Ala Ser Glu Glu Ile Thr Val Gly Asp
    210                 215                 220

Ala Val Leu Ser Ser Ile Gln Val Thr Ser Asn Ser Pro Asn Ile Pro
225                 230                 235                 240

Leu Gly Lys Lys Gln Lys Leu Thr Ala Thr Gly Ile Tyr Ser Asp Asn
                245                 250                 255

Ser Asn Arg Asp Ile Ser Ser Ser Val Ile Trp Asn Ser Ser Asn Ser
            260                 265                 270

Thr Ile Ala Asn Ile Gln Asn Asn Gly Ile Leu Glu Thr Ala Asp Thr
        275                 280                 285

Gly Ile Val Thr Val Ser Ala Ser Arg Gly Asn Ile Asn Gly Ser Ile
    290                 295                 300

Lys Leu Ile Val Thr Pro Ala Ala Leu Val Ser Ile Ser Val Ser Pro
305                 310                 315                 320

Thr Asn Ser Ala Val Ala Lys Gly Leu Gln Glu Asn Phe Lys Ala Thr
                325                 330                 335

Gly Ile Phe Thr Asp Asn Ser Asn Ser Asp Ile Thr Asp Gln Val Thr
            340                 345                 350

Trp Asp Ser Ser Asn Pro Asp Ile Leu Ser Ile Ser Asn Ala Ser Asp
        355                 360                 365

Ser His Gly Leu Ala Ser Thr Leu Asn Gln Gly Asn Val Lys Val Thr
    370                 375                 380

Ala Ser Ile Gly Gly Ile Gln Gly Ser Thr Asp Phe Lys Val Thr Gln
385                 390                 395                 400

Glu Val Leu Thr Ser Ile Glu Val Ser Pro Val Leu Pro Ser Ile Ala
                405                 410                 415

Lys Gly Leu Thr Gln Lys Phe Thr Ala Ile Gly Ile Phe Thr Asp Asn
            420                 425                 430

Ser Lys Lys Asp Ile Thr Asn Gln Val Thr Trp Asn Ser Ser Ser Ala
        435                 440                 445

Ile Ala Ser Val Ser Asn Leu Asp Asp Asn Lys Gly Leu Gly Lys Ala
    450                 455                 460

His Ala Val Gly Asp Thr Thr Ile Thr Ala Thr Leu Gly Lys Val Ser
465                 470                 475                 480

Gly Lys Thr Trp Phe Thr Val Val Pro Ala Val Leu Thr Ser Ile Gln
                485                 490                 495

Ile Asn Pro Val Asn Pro Ser Leu Ala Lys Gly Leu Thr Gln Lys Phe
            500                 505                 510

Thr Ala Thr Gly Ile Tyr Ser Asp Asn Ser Asn Lys Asp Ile Thr Ser
        515                 520                 525

Ser Val Thr Trp Phe Ser Ser Asp Ser Ser Ile Ala Thr Ile Ser Asn
    530                 535                 540

Ala Lys Lys Asn Gln Gly Asn Ser Tyr Gly Ala Ala Thr Gly Ala Thr
```

-continued

```
545                 550                 555                 560

Asp Ile Lys Ala Thr Phe Gly Lys Val Ser Ser Pro Val Ser Thr Leu
                565                 570                 575

Ser Val Thr Ala Ala Lys Leu Val Glu Ile Gln Ile Thr Pro Ala Ala
            580                 585                 590

Ala Ser Lys Ala Lys Gly Ile Ser Glu Arg Phe Lys Ala Thr Gly Ile
        595                 600                 605

Phe Thr Asp Asn Ser Asn Ser Asp Ile Thr Asn Gln Val Thr Trp Ser
    610                 615                 620

Ser Ser Asn Thr Asp Ile Leu Thr Val Ser Asn Thr Asn Ala Lys Arg
625                 630                 635                 640

Gly Leu Gly Ser Thr Leu Lys Gln Gly Thr Val Lys Val Ile Ala Ser
                645                 650                 655

Met Gly Gly Ile Glu Ser Ser Val Asp Phe Thr Val Thr Gln Ala Asn
            660                 665                 670

Leu Thr Ser Ile Glu Val Ser Pro Thr Arg Ser Ser Ile Ala Lys Gly
        675                 680                 685

Leu Thr Gln Lys Phe Thr Ala Ile Gly Ile Phe Thr Asp His Ser Lys
    690                 695                 700

Lys Asp Ile Thr Glu Gln Val Thr Trp Lys Ser Ser Ser Lys Val Leu
705                 710                 715                 720

Asn Met Leu Asn Ala Ser Gly Glu Glu Gly Arg Gly Lys Ala Ile Ser
                725                 730                 735

Val Gly Lys Ala Thr Ile Thr Ala Thr Leu Glu Lys Leu Ser Gly Lys
            740                 745                 750

Ala Asp Ile Thr Val Thr Pro Ala Val Leu Thr Ser Ile Gln Ile Ser
        755                 760                 765

Pro Val Lys Pro Ser Leu Val Lys Gly Leu Thr Glu Asn Phe Ser Ala
    770                 775                 780

Thr Gly Ile Tyr Ser Asp Asn Ser Ser Lys Asp Ile Thr Ser Ser Val
785                 790                 795                 800

Thr Trp His Ser Phe Asn Asn Ser Val Ala Thr Ile Ser Asn Thr Lys
                805                 810                 815

Asn Tyr His Gly Gln Ala His Ala Thr Gly Thr Gly Ile Val Gly Ile
            820                 825                 830

Lys Ala Thr Leu Gly Asn Val Ser Ser Pro Val Ser Lys Leu Ser Val
        835                 840                 845

Thr Ala Ala Glu Leu Val Glu Ile Val Leu Asn Pro Thr Leu Ser His
    850                 855                 860

Lys Ala Lys Gly Leu Thr Glu Asn Phe Lys Ala Thr Gly Val Phe Thr
865                 870                 875                 880

Asp Asn Ser Thr Lys Asp Ile Thr Asp Gln Val Thr Trp Lys Ser Ser
                885                 890                 895

Asn Thr Ala Tyr Ala Glu Ile Ser Asn Ala Thr Gly Ser Lys Gly Val
            900                 905                 910

Val Asn Ala Leu Ser Lys Gly Thr Ser His Ile Ser Ala Thr Leu Gly
        915                 920                 925

Ser Ile Ser Ser Ala Asn Ala Thr Phe Gln Val Thr Pro Ala Lys Ile
    930                 935                 940

Ala Ser Ile Glu Ile Thr Pro Asn Asn Phe Phe Leu Ile Lys Lys Leu
945                 950                 955                 960

Ser Tyr Pro Phe Lys Ala Ile Gly Ile Tyr Thr Asp Asn Thr Lys Thr
                965                 970                 975
```

Asp Ile Thr Lys Gln Val Ser Trp Ser Ser Ser Asp Pro Asn Val Ala
980 985 990

Ser Ile Asp Asn Thr Phe Ser Leu Ala Gly Ser Ala Thr Ala Ile Asp
995 1000 1005

Asp Gly Lys Thr Asn Ile Thr Ala Thr Leu Ser Asp Ser Met Ser
1010 1015 1020

Ala Ser Thr Thr Leu Tyr Val Thr Ser Ala Thr Leu Val Asp Ile
1025 1030 1035

Glu Val Lys Pro Ser Ile Phe Val Leu Ser Glu Gly Leu Thr Leu
1040 1045 1050

Gln Leu Thr Ala Thr Gly Ile Tyr Ser Asp Tyr Ser Thr Tyr Asp
1055 1060 1065

Leu Thr Gln Val Val Thr Trp Thr Ser Ser Glu Pro Ser Asn Ile
1070 1075 1080

Ser Ile Glu Asn Thr Ala Gly Lys Lys Gly Lys Val Thr Ala Leu
1085 1090 1095

Ala Phe Gly Ala Ser Glu Phe Thr Ala Thr Tyr Asp Ser Ile Glu
1100 1105 1110

Ser Asn Arg Ala Trp Ile Phe Val Asn Asp Glu Lys Phe Val Asn
1115 1120 1125

Ile Thr Ile Ser Ser Ser Gln Val Leu Thr Asp Lys Gly Leu Thr
1130 1135 1140

Gln Gln Phe Lys Ala Ile Gly Thr Phe Glu Lys Gly Ser Glu Leu
1145 1150 1155

Asp Leu Thr Asp Leu Val Thr Trp Lys Ser Ser Asp Ser Lys Val
1160 1165 1170

Ala Ser Ile Gly Asn Ser Asn Asp Asp Arg Gly Leu Ile Thr Pro
1175 1180 1185

Leu Ser Val Gly Ser Ser Lys Ile Ser Ala Thr Tyr Asn Ser Ile
1190 1195 1200

His Ser Asn Ser Ile Asp Phe Glu Val Thr Pro Glu Ile Leu Ala
1205 1210 1215

Ser Ile Lys Thr Lys Pro
1220

<210> SEQ ID NO 3
<211> LENGTH: 5863
<212> TYPE: DNA
<213> ORGANISM: Leptospira kirschneri

<400> SEQUENCE: 3
atgcctaaac atatcaacaa actcagagat aaaaaaacgt ggccttttct tcagtttatt 60
tttattcttt ttctaacatt cagcctattt tttttggaaa gttgcgcggc ttggccaatt 120
ttttcaggca cacctggttt attagcaggt aaaaaaagcg gagcaaacaa ttcactttgg 180
atgctttttt taggaataga taatccgctc gaatcggagc catccgaagc agagttagat 240
cggatcgaaa tttccgtacc gaactcaaat ttagctcgag gtactacttt acatctaaac 300
gccacagcca tctataaaga caatactcac cgagatattt cttcggaagg atcctggtcc 360
tctacggatt cgagcattct caagctatta acacaatctc aattcaaagg aatgaatcta 420
ggttctggaa acgttaatgt atcctttcaa ggaaaaaacg caactacaac gttaaccgtt 480
acatccgctg ttttgtccga tctgaccgta acttgtgtga accaaggtag tccattacct 540
gttggaatcg atcgtcaatg taaattagaa ggaatttttt cggacggtag tactcaggtt 600
ttaacttccg atccaagcgc gtcctggaac gtaacccaat cttctattgc aggtgtaaac 660
accacaggtt tagtttccgg actttctcca ggtaacactt ttattaccac ttcttatgga 720
agtaaaacct ccagtttgaa tgtgaccgta agtgcggcaa cccttagctc gatctcagtg 780
actcctgcca actcaagtta tcctcttggc aaggtccaac agtacacagc aatcggaacc 840
tacagcaatc agtccactca agatttaaca aatcaggttt cctgggcttc tttaaatact 900
tccgttgcta cgatcgataa ttctacatcc gccaaaggta tgcttactac tcaatcaacc 960
ggttcagcaa acatcacggc aacgttaggc ggaattaccg gacagactac tagtaaacgt 1020
cacttccgca gttcttacta gtattacgat cactcctgca aatccaagcg tagccaatgg 1080
aaggacatta tatcttaccg ccaccggagt tttttcggat ggtacagttt ccgacattac 1140
caaccaagta acttggtcca gttccttaac aagtgtagct accgcagata actcaggcgg 1200
tttatccgga agaatttccg gagtcggagt tggtagtacg aatatcaccg ccgccatcgg 1260
tggagtagat attacggttt ctttaaatgt taccaacgcc actttagaat cgattcaagt 1320
ggtttccgat tcccattcga tagctcgagg tacgtctacg tttgtacaag cgataggagt 1380
ctactcggac ggttcttctc aaaacataag tgatcaagtt gcctggaaca gctctaattc 1440
ttcaatatta caaatatcta atttaaatgc agttcccaaa agagaaatac aatctccttc 1500
ttccggaggc ctaggtacag caaggatcac cgcaacttta gaagcaatct cctcatatac 1560
cgacatctcg gtcaatgcag caactttagt ttctatcgaa gtgtcaccca caaatccttc 1620
ggtatcttca ggacttaccg ttccttttac ggcgaccgga gtttatacgg atggaagtaa 1680
tcaaaatctg acttctcaag taacttggaa ttcctccaac acgaacagag ctacaatcag 1740
caacgcaaac ggaactcaag gaattgcctt gggctcttct gtcggaacta cgaacatatc 1800
agcaacgtta ggtgcggtta cttcttccgc taccactctt acggtcacaa acgcggtttt 1860
aaattcgatc acgattactc cgtctcttcc ttccgtagca gtaggaagaa gtctgaacct 1920
tactgcaacc ggaacttatt ctgacggaag taaccaagat ttaactacct ccgtcgcttg 1980
gacgagtacg gattcttcca tcgtttccgt agacaacgcc tcaggtagac aggggcagac 2040
gacaggtgtt gcacaaggta acactcagat cagtgccaca ttaggcggaa cttcttctgc 2100
tatcaatttt acggtaagtg cagcggtttt agattcaatt caagtaactc tggaagattc 2160
tccgattgca aaaggaactt ctacaagagc aatcgcgacg ggtgtttttt cagacggaag 2220
caatttgaat attagtgatc aagttatttg ggatagttca caaacaaacg tgatccagct 2280
aggagtttta gaaaccggtc ctaaaaagaa actgatgaat tctcccgcaa atggaaacag 2340
taccactgga acctcaagga tcactgcaac gttaggaggt gtgagcggat acgccgatct 2400
tacagtaatc gctccaagtt taaccagcat tcaaatcgat cctacacatc cgagcgttgc 2460
caacggtctg actcaaaatt ttactgcaac cggagtttac tcagatggta gcaatcagaa 2520
tctaaccgat tccgttactt gggcgtcttc caatcctgct gttgccacga tcagcaacgc 2580
ttccggaacc aacggtaaag ctactactct tcaaactgga tccaccaata tcagcgcgag 2640
tctgggcgcc actacttctg atccaagtgt attaacggtt acaaacgcaa ccttaacaag 2700
tatcacgatc gctcccacct cttccttcaa catcgcaaaa ggattaaatc aagactttgt 2760
agcgaccggt tattatacag atggttcttc tagagacctg accactcaag tcacttggaa 2820
ttcttccaat acttctaccg ctacgatcag caatgcaaac ggaactcaag gaagaatggc 2880
cgcggtcgat actggttcta caaatatctc cgcgtcttta ggaggaacgt atagtcagac 2940

-continued

```
cacaaacgta accgttacat ctgcggttct gaattcgatc caggtttctc cagcggacat   3000
tagtgtagcc aaaggaaaca ccaaggccta caccgcgatc ggagtatatt cagattttag   3060
cacgttagac gttacttctc aggttacctg gacttcttcc agcgtttcga tcgctacgat   3120
cagcaatgca agcggacacg aaggtttagc tacggctgta ggcacgggaa cttccacaat   3180
taccgcaact cttggaggaa tttctaattc tacgagtttg acggttacgg ccgccgtatt   3240
ggtttctctt tcggtaggtc ctaccaatag ttttgtttat atgacacaaa ccaaaaattt   3300
tatggctact ggaacgtatt ctgacggaac gatgcaggat cttacaactc aagtcacctg   3360
gacttcttcc gatacaacct tgggaacaat cagcaacgcc ttcggaatag aaggtagggc   3420
tacaggaatt gctgccggtg ccataacgat cactgcgact ttgggaagta tcagcggaaa   3480
cacttctttg actataatct ttttagatac gatagcacct gcgatcacaa acgtagtcgc   3540
cttaactcct actactttaa gaattacata ttccgaaaac gtaaacgaaa cccaggcaaa   3600
aaccgcggcc aattacaaac tggctcttac ttcttccgta accggaagtt gttcagataa   3660
cagcaacttt acttctacct cttctgtgat tactgtttcc tcagtgagtg gaagcggatc   3720
tgtgtttgtt ctaactctag gttcttcaca aacgtctaac gcaccttata cgattttagt   3780
gaataaatcg ggaatacaag atctttctac aaccccaaac aatttgggtt gtgcaaacta   3840
cggagacttc ttaggacagg aacaaatcaa aatcgtatcc gcctcctgtg caaattccaa   3900
ttccgtgatt ttgaatttct ctaaggctcc taaatctgga aacaatgtcg ccggttccgc   3960
agaatgtacc ggttctgcag aatgttctaa tcgttacaaa atttccggag caagcgatct   4020
tggaacaatt aacagcgtaa aggtgttaga tggaattatt tgtaacggag caactgcaga   4080
ttccgcaaaa gtatgcgtaa ttcataattt agtacaaacc ggagcacaat atacaatcat   4140
cactgcggat tccgtagacg gagacggatt tgacaactca agctggggat caatccgaaa   4200
ttctttggat acagagaatc ttcaatcttc tcccagagac agggcttcct ttttaggatg   4260
tggaacgtct ccggtcaact ttgcagacgg accgatttcc atcgatccaa actcatccac   4320
gttcggttat ctaatcgatt ttaactctaa gatctattca ggaccaaaca attccgggaa   4380
cggagcgctt cgatttgcct atgatggaag tgttccagaa tcagttcaat tctcctttga   4440
aaaagacaca accgttcaag acggtgacgc gactaacgta agttcaaact cagcttcttc   4500
cagagagaat tcgatctcgg ttccgcctta cgttacatta ggacactccg gatgtactac   4560
aaacaacgga actctttctc taggatgtgg tccggataac gaaaacggaa gaggagtatt   4620
cgctactgga attctttcca gcgtctccta tctatttgtt gcagctgcaa aaaccgtagc   4680
ggacggcctg ggacaatact tatttgatta tctgtattac tccgcagaca cttctactaa   4740
tacaagtttc aaatatatag atctaggatc gatcaccgga actttaaccg ccggaacttc   4800
ttcgcttact gtactcaata atagagtgtt tgcaggtttt gcaaagtcaa gcaacgacgg   4860
aatcggattg ttcggaggac ttaatgcacc cgattttgga tttgtaacgt ttaactcagc   4920
ggactcagga actggatttt gtactccagg ctccaactgc gacgcgtttg acggaaccaa   4980
aggaaaaaga atccggatcg atttccttcc ttacttcgga ggaccgtcca ccggtttatt   5040
aggaattaat aataatgcac atccaaactg ggcgtattat atcggagtcg attccatgtt   5100
cgtatttaaa aatcgtatct atgccgcaaa cggaggatta cacgcggtag gacataacgg   5160
ttccataata cgttctacaa ctgcagatcc aaccgcggct tgtaccggac cggactcttg   5220
ttctaactgg gtggaaattg gacctagaac caacacgaaa tggcacaaca gtcccacaaa   5280
caactggttc tctttagagt taaatcaatt ttacaatctg attccgggag ataaggcgtt   5340
```

-continued

```
tgcacaattt gccgagttca acaataacct ttatgtaact agaaccattt gtattcaaag   5400

ttctcaagcg actggaatca gaaccaatcc aggaaccgta acaggatgta cagacggaac   5460

aactacaaat cgaagggcac aactttggaa atgtgatcct acaatttcag gaaacacgag   5520

cgaatgtgat gcagcggatt ggtcggtcgt aggcgacgac ggaaccggaa tcacaaacat   5580

gggagattct acaaaccgaa cgatcaccat ggtgatgaaa aacggatcct atctttacat   5640

aggatatgat aatccaaacg gaatcagaat ttatagaacc aacgtagcca acccgggatc   5700

atcctctgcg tcttggagtc aaatcgccgg gaacggtctc acagatgcga ctaacgttca   5760

acaaatttac tcggccgtat ccgtaccttc cggaagtatc aattatatct acgtaagcgc   5820

tggaaaaagt aacgtttctg ttcggacgta tcgtcaacaa aat                     5863
```

<210> SEQ ID NO 4
<211> LENGTH: 1954
<212> TYPE: PRT
<213> ORGANISM: Leptospira kirschneri

<400> SEQUENCE: 4

```
Met Pro Lys His Ile Asn Lys Leu Arg Asp Lys Lys Thr Trp Pro Phe
1               5                   10                  15

Leu Gln Phe Ile Phe Ile Leu Phe Leu Thr Phe Ser Leu Phe Phe Leu
            20                  25                  30

Glu Ser Cys Ala Ala Trp Pro Ile Phe Ser Gly Thr Pro Gly Leu Leu
        35                  40                  45

Ala Gly Lys Lys Ser Gly Ala Asn Asn Ser Leu Trp Met Leu Phe Leu
    50                  55                  60

Gly Ile Asp Asn Pro Leu Glu Ser Glu Pro Ser Glu Ala Glu Leu Asp
65                  70                  75                  80

Arg Ile Glu Ile Ser Val Pro Asn Ser Asn Leu Ala Arg Gly Thr Thr
                85                  90                  95

Leu His Leu Asn Ala Thr Ala Ile Tyr Lys Asp Asn Thr His Arg Asp
            100                 105                 110

Ile Ser Ser Glu Gly Ser Trp Ser Ser Thr Asp Ser Ser Ile Leu Lys
        115                 120                 125

Leu Leu Thr Gln Ser Gln Phe Lys Gly Met Asn Leu Gly Ser Gly Asn
    130                 135                 140

Val Asn Val Ser Phe Gln Gly Lys Asn Ala Thr Thr Thr Leu Thr Val
145                 150                 155                 160

Thr Ser Ala Val Leu Ser Asp Leu Thr Val Thr Cys Val Asn Gln Gly
                165                 170                 175

Ser Pro Leu Pro Val Gly Ile Asp Arg Gln Cys Lys Leu Glu Gly Ile
            180                 185                 190

Phe Ser Asp Gly Ser Thr Gln Val Leu Thr Ser Asp Pro Ser Ala Ser
        195                 200                 205

Trp Asn Val Thr Gln Ser Ser Ile Ala Gly Val Asn Thr Thr Gly Leu
    210                 215                 220

Val Ser Gly Leu Ser Pro Gly Asn Thr Phe Ile Thr Thr Ser Tyr Gly
225                 230                 235                 240

Ser Lys Thr Ser Ser Leu Asn Val Thr Val Ser Ala Ala Thr Leu Ser
                245                 250                 255

Ser Ile Ser Val Thr Pro Ala Asn Ser Ser Tyr Pro Leu Gly Lys Val
            260                 265                 270

Gln Gln Tyr Thr Ala Ile Gly Thr Tyr Ser Asn Gln Ser Thr Gln Asp
```

-continued

```
        275                 280                 285

Leu Thr Asn Gln Val Ser Trp Ala Ser Leu Asn Thr Ser Val Ala Thr
    290                 295                 300

Ile Asp Asn Ser Thr Ser Ala Lys Gly Met Leu Thr Thr Gln Ser Thr
305                 310                 315                 320

Gly Ser Ala Asn Ile Thr Ala Thr Leu Gly Gly Ile Thr Gly Gln Thr
                325                 330                 335

Thr Val Asn Val Thr Ser Ala Val Leu Thr Ser Ile Thr Ile Thr Pro
            340                 345                 350

Ala Asn Pro Ser Val Ala Asn Gly Arg Thr Leu Tyr Leu Thr Ala Thr
        355                 360                 365

Gly Val Phe Ser Asp Gly Thr Val Ser Asp Ile Thr Asn Gln Val Thr
    370                 375                 380

Trp Ser Ser Ser Leu Thr Ser Val Ala Thr Ala Asp Asn Ser Gly Gly
385                 390                 395                 400

Leu Ser Gly Arg Ile Ser Gly Val Gly Val Gly Ser Thr Asn Ile Thr
                405                 410                 415

Ala Ala Ile Gly Gly Val Asp Ile Thr Val Ser Leu Asn Val Thr Asn
            420                 425                 430

Ala Thr Leu Glu Ser Ile Gln Val Val Ser Asp Ser His Ser Ile Ala
        435                 440                 445

Arg Gly Thr Ser Thr Phe Val Gln Ala Ile Gly Val Tyr Ser Asp Gly
    450                 455                 460

Ser Ser Gln Asn Ile Ser Asp Gln Val Ala Trp Asn Ser Ser Asn Ser
465                 470                 475                 480

Ser Ile Leu Gln Ile Ser Asn Leu Asn Ala Val Pro Lys Arg Glu Ile
                485                 490                 495

Gln Ser Pro Ser Ser Gly Gly Leu Gly Thr Ala Arg Ile Thr Ala Thr
            500                 505                 510

Leu Glu Ala Ile Ser Ser Tyr Thr Asp Ile Ser Val Asn Ala Ala Thr
        515                 520                 525

Leu Val Ser Ile Glu Val Ser Pro Thr Asn Pro Ser Val Ser Ser Gly
    530                 535                 540

Leu Thr Val Pro Phe Thr Ala Thr Gly Val Tyr Thr Asp Gly Ser Asn
545                 550                 555                 560

Gln Asn Leu Thr Ser Gln Val Thr Trp Asn Ser Ser Asn Thr Asn Arg
                565                 570                 575

Ala Thr Ile Ser Asn Ala Asn Gly Thr Gln Gly Ile Ala Leu Gly Ser
            580                 585                 590

Ser Val Gly Thr Thr Asn Ile Ser Ala Thr Leu Gly Ala Val Thr Ser
        595                 600                 605

Ser Ala Thr Thr Leu Thr Val Thr Asn Ala Val Leu Asn Ser Ile Thr
    610                 615                 620

Ile Thr Pro Ser Leu Pro Ser Val Ala Val Gly Arg Ser Leu Asn Leu
625                 630                 635                 640

Thr Ala Thr Gly Thr Tyr Ser Asp Gly Ser Asn Gln Asp Leu Thr Thr
                645                 650                 655

Ser Val Ala Trp Thr Ser Thr Asp Ser Ser Ile Val Ser Val Asp Asn
            660                 665                 670

Ala Ser Gly Arg Gln Gly Gln Thr Thr Gly Val Ala Gln Gly Asn Thr
        675                 680                 685

Gln Ile Ser Ala Thr Leu Gly Gly Thr Ser Ser Ala Ile Asn Phe Thr
    690                 695                 700
```

```
Val Ser Ala Ala Val Leu Asp Ser Ile Gln Val Thr Leu Glu Asp Ser
705                 710                 715                 720

Pro Ile Ala Lys Gly Thr Ser Thr Arg Ala Ile Ala Thr Gly Val Phe
                725                 730                 735

Ser Asp Gly Ser Asn Leu Asn Ile Ser Asp Gln Val Ile Trp Asp Ser
            740                 745                 750

Ser Gln Thr Asn Val Ile Gln Leu Gly Val Leu Glu Thr Gly Pro Lys
        755                 760                 765

Lys Lys Leu Met Asn Ser Pro Ala Asn Gly Asn Ser Thr Thr Gly Thr
    770                 775                 780

Ser Arg Ile Thr Ala Thr Leu Gly Gly Val Ser Gly Tyr Ala Asp Leu
785                 790                 795                 800

Thr Val Ile Ala Pro Ser Leu Thr Ser Ile Gln Ile Asp Pro Thr His
                805                 810                 815

Pro Ser Val Ala Asn Gly Leu Thr Gln Asn Phe Thr Ala Thr Gly Val
            820                 825                 830

Tyr Ser Asp Gly Ser Asn Gln Asn Leu Thr Asp Ser Val Thr Trp Ala
        835                 840                 845

Ser Ser Asn Pro Ala Val Ala Thr Ile Ser Asn Ala Ser Gly Thr Asn
    850                 855                 860

Gly Lys Ala Thr Thr Leu Gln Thr Gly Ser Thr Asn Ile Ser Ala Ser
865                 870                 875                 880

Leu Gly Ala Thr Thr Ser Asp Pro Ser Val Leu Thr Val Thr Asn Ala
                885                 890                 895

Thr Leu Thr Ser Ile Thr Ile Ala Pro Thr Ser Ser Phe Asn Ile Ala
            900                 905                 910

Lys Gly Leu Asn Gln Asp Phe Val Ala Thr Gly Tyr Tyr Thr Asp Gly
        915                 920                 925

Ser Ser Arg Asp Leu Thr Thr Gln Val Thr Trp Asn Ser Ser Asn Thr
    930                 935                 940

Ser Thr Ala Thr Ile Ser Asn Ala Asn Gly Thr Gln Gly Arg Met Ala
945                 950                 955                 960

Ala Val Asp Thr Gly Ser Thr Asn Ile Ser Ala Ser Leu Gly Gly Thr
                965                 970                 975

Tyr Ser Gln Thr Thr Asn Val Thr Val Thr Ser Ala Val Leu Asn Ser
            980                 985                 990

Ile Gln Val Ser Pro Ala Asp Ile  Ser Val Ala Lys Gly  Asn Thr Lys
        995                 1000                1005

Ala Tyr  Thr Ala Ile Gly Val  Tyr Ser Asp Phe Ser  Thr Leu Asp
    1010                1015                1020

Val Thr  Ser Gln Val Thr Trp  Thr Ser Ser Ser Val  Ser Ile Ala
    1025                1030                1035

Thr Ile  Ser Asn Ala Ser Gly  His Glu Gly Leu Ala  Thr Ala Val
    1040                1045                1050

Gly Thr  Gly Thr Ser Thr Ile  Thr Ala Thr Leu Gly  Gly Ile Ser
    1055                1060                1065

Asn Ser  Thr Ser Leu Thr Val  Thr Ala Ala Val Leu  Val Ser Leu
    1070                1075                1080

Ser Val  Gly Pro Thr Asn Ser  Phe Val Tyr Met Thr  Gln Thr Lys
    1085                1090                1095

Asn Phe  Met Ala Thr Gly Thr  Tyr Ser Asp Gly Thr  Met Gln Asp
    1100                1105                1110
```

-continued

```
Leu Thr  Thr Gln Val Thr Trp  Thr Ser Ser Asp Thr  Thr Leu Gly
    1115                 1120                 1125

Thr Ile  Ser Asn Ala Phe Gly  Ile Glu Gly Arg Ala  Thr Gly Ile
    1130                 1135                 1140

Ala Ala  Gly Ala Ile Thr Ile  Thr Ala Thr Leu Gly  Ser Ile Ser
    1145                 1150                 1155

Gly Asn  Thr Ser Leu Thr Ile  Ile Phe Leu Asp Thr  Ile Ala Pro
    1160                 1165                 1170

Ala Ile  Thr Asn Val Val Ala  Leu Thr Pro Thr Thr  Leu Arg Ile
    1175                 1180                 1185

Thr Tyr  Ser Glu Asn Val Asn  Glu Thr Gln Ala Lys  Thr Ala Ala
    1190                 1195                 1200

Asn Tyr  Lys Leu Ala Leu Thr  Ser Ser Val Thr Gly  Ser Cys Ser
    1205                 1210                 1215

Asp Asn  Ser Asn Phe Thr Ser  Thr Ser Ser Val Ile  Thr Val Ser
    1220                 1225                 1230

Ser Val  Ser Gly Ser Gly Ser  Val Phe Val Leu Thr  Leu Gly Ser
    1235                 1240                 1245

Ser Gln  Thr Ser Asn Ala Pro  Tyr Thr Ile Leu Val  Asn Lys Ser
    1250                 1255                 1260

Gly Ile  Gln Asp Leu Ser Thr  Thr Pro Asn Asn Leu  Gly Cys Ala
    1265                 1270                 1275

Asn Tyr  Gly Asp Phe Leu Gly  Gln Glu Gln Ile Lys  Ile Val Ser
    1280                 1285                 1290

Ala Ser  Cys Ala Asn Ser Asn  Ser Val Ile Leu Asn  Phe Ser Lys
    1295                 1300                 1305

Ala Pro  Lys Ser Gly Asn Asn  Val Ala Gly Ser Ala  Glu Cys Thr
    1310                 1315                 1320

Gly Ser  Ala Glu Cys Ser Asn  Arg Tyr Lys Ile Ser  Gly Ala Ser
    1325                 1330                 1335

Asp Leu  Gly Thr Ile Asn Ser  Val Lys Val Leu Asp  Gly Ile Ile
    1340                 1345                 1350

Cys Asn  Gly Ala Thr Ala Asp  Ser Ala Lys Val Cys  Val Ile His
    1355                 1360                 1365

Asn Leu  Val Gln Thr Gly Ala  Gln Tyr Thr Ile Ile  Thr Ala Asp
    1370                 1375                 1380

Ser Val  Asp Gly Asp Gly Phe  Asp Asn Ser Ser Trp  Gly Ser Ile
    1385                 1390                 1395

Arg Asn  Ser Leu Asp Thr Glu  Asn Leu Gln Ser Ser  Pro Arg Asp
    1400                 1405                 1410

Arg Ala  Ser Phe Leu Gly Cys  Gly Thr Ser Pro Val  Asn Phe Ala
    1415                 1420                 1425

Asp Gly  Pro Ile Ser Ile Asp  Pro Asn Ser Ser Thr  Phe Gly Tyr
    1430                 1435                 1440

Leu Ile  Asp Phe Asn Ser Lys  Ile Tyr Ser Gly Pro  Asn Asn Ser
    1445                 1450                 1455

Gly Asn  Gly Ala Leu Arg Phe  Ala Tyr Asp Gly Ser  Val Pro Glu
    1460                 1465                 1470

Ser Val  Gln Phe Ser Phe Glu  Lys Asp Thr Thr Val  Gln Asp Gly
    1475                 1480                 1485

Asp Ala  Thr Asn Val Ser Ser  Asn Ser Ala Ser Ser  Arg Glu Asn
    1490                 1495                 1500

Ser Ile  Ser Val Pro Pro Tyr  Val Thr Leu Gly His  Ser Gly Cys
```

-continued

```
    1505                1510                1515

Thr Thr  Asn Asn Gly Thr Leu  Ser Leu Gly Cys Gly  Pro Asp Asn
    1520                1525                1530

Glu Asn  Gly Arg Gly Val Phe  Ala Thr Gly Ile Leu  Ser Ser Val
    1535                1540                1545

Ser Tyr  Leu Phe Val Ala Ala  Ala Lys Thr Val Ala  Asp Gly Leu
    1550                1555                1560

Gly Gln  Tyr Leu Phe Asp Tyr  Leu Tyr Tyr Ser Ala  Asp Thr Ser
    1565                1570                1575

Thr Asn  Thr Ser Phe Lys Tyr  Ile Asp Leu Gly Ser  Ile Thr Gly
    1580                1585                1590

Thr Leu  Thr Ala Gly Thr Ser  Ser Leu Thr Val Leu  Asn Asn Arg
    1595                1600                1605

Val Phe  Ala Gly Phe Ala Lys  Ser Ser Asn Asp Gly  Ile Gly Leu
    1610                1615                1620

Phe Gly  Gly Leu Asn Ala Pro  Asp Phe Gly Phe Val  Thr Phe Asn
    1625                1630                1635

Ser Ala  Asp Ser Gly Thr Gly  Phe Cys Thr Pro Gly  Ser Asn Cys
    1640                1645                1650

Asp Ala  Phe Asp Gly Thr Lys  Gly Lys Arg Ile Arg  Ile Asp Phe
    1655                1660                1665

Leu Pro  Tyr Phe Gly Gly Pro  Ser Thr Gly Leu Leu  Gly Ile Asn
    1670                1675                1680

Asn Asn  Ala His Pro Asn Trp  Ala Tyr Tyr Ile Gly  Val Asp Ser
    1685                1690                1695

Met Phe  Val Phe Lys Asn Arg  Ile Tyr Ala Ala Asn  Gly Gly Leu
    1700                1705                1710

His Ala  Val Gly His Asn Gly  Ser Ile Ile Arg Ser  Thr Thr Ala
    1715                1720                1725

Asp Pro  Thr Ala Ala Cys Thr  Gly Pro Asp Ser Cys  Ser Asn Trp
    1730                1735                1740

Val Glu  Ile Gly Pro Arg Thr  Asn Thr Lys Trp His  Asn Ser Pro
    1745                1750                1755

Thr Asn  Asn Trp Phe Ser Leu  Glu Leu Asn Gln Phe  Tyr Asn Leu
    1760                1765                1770

Ile Pro  Gly Asp Lys Ala Phe  Ala Gln Phe Ala Glu  Phe Asn Asn
    1775                1780                1785

Asn Leu  Tyr Val Thr Arg Thr  Ile Cys Ile Gln Ser  Ser Gln Ala
    1790                1795                1800

Thr Gly  Ile Arg Thr Asn Pro  Gly Thr Val Thr Gly  Cys Thr Asp
    1805                1810                1815

Gly Thr  Thr Thr Asn Arg Arg  Ala Gln Leu Trp Lys  Cys Asp Pro
    1820                1825                1830

Thr Ile  Ser Gly Asn Thr Ser  Glu Cys Asp Ala Ala  Asp Trp Ser
    1835                1840                1845

Val Val  Gly Asp Asp Gly Thr  Gly Ile Thr Asn Met  Gly Asp Ser
    1850                1855                1860

Thr Asn  Arg Thr Ile Thr Met  Val Met Lys Asn Gly  Ser Tyr Leu
    1865                1870                1875

Tyr Ile  Gly Tyr Asp Asn Pro  Asn Gly Ile Arg Ile  Tyr Arg Thr
    1880                1885                1890

Asn Val  Ala Asn Pro Gly Ser  Ser Ser Ala Ser Trp  Ser Gln Ile
    1895                1900                1905
```

```
Ala Gly Asn Gly Leu Thr Asp Ala Thr Asn Val Gln Gln Ile Tyr
    1910                1915                1920

Ser Ala Val Ser Val Pro Ser Gly Ser Ile Asn Tyr Ile Tyr Val
    1925                1930                1935

Ser Ala Gly Lys Ser Asn Val Ser Val Arg Thr Tyr Arg Gln Gln
    1940                1945                1950

Asn


<210> SEQ ID NO 5
<211> LENGTH: 5658
<212> TYPE: DNA
<213> ORGANISM: Leptospira kirschneri

<400> SEQUENCE: 5

atgaagagaa cattttgtat ttcgattctt ctttcgatgt tttttcaaag ttgtatgtct     60
tggccacttt taaccagtct cgcgggttta gcagctggta aaaaaagtaa tgggctgccc    120
tttttccacc ttctattaag taactctgat ccagttatta caaggatcga gctcagttat    180
caaaattctt ccatcgcaaa aggtacaagt acaactctcg aagtcaccgc aatctttgat    240
aacggaacaa atcagaatat tacggattcg acatctatcg tttccgatgc ccaatcaatc    300
gttgacattc aaggtaacag agtcagagga atcgcttctg gttcttccat tataaaagct    360
gaatacaacg ggatgtattc tgaacaaaaa attacggtta caccagccac gataaactca    420
attcaagtta cgagtttaga tgacggtata ttacctaaag gtacaaatcg tcaatttgct    480
gccatcggta tcttttcgga tggttctcat caagatattt ccaacgatcc attgatcgtt    540
tggtcttcca gtaatataga tttagttcga gtagatgatt ccggtttggc ctcaggtatc    600
aatttaggaa cggctcatat tcgtgcatcc tttcaatcaa aacaagcctc cgaagagata    660
actgttggtg acgctgttct ttcttctatc caagtaactt ccaacagtcc aaatattcct    720
ctcggaaaaa aacaaaaact cacagctact ggaatttatt cggataactc taacagggat    780
atttcctctt ctgttatctg gaattcttct aattccacta tcgctaatat tcagaataac    840
ggaatattag aaacagctga tactggaatt gttactgttt ctgcttctag aggtaatata    900
aatggttcca taaaactaat cgtcactcct gctgccttag tttctatttc tgtttctcct    960
acaaattctg cagtagcaaa aggtttacaa gaaaacttta aagctacagg gatctttaca   1020
gataattcga actcagatat tacagatcaa gttacttggg attcttctaa tccggatatt   1080
ctttccattt ccaatgcaag tgatagccac gggttagctt ccacactcaa ccaaggaaat   1140
gttaaggtca ccgcttccat cggtggaata caaggatcca ctgattttaa agttacacaa   1200
gaggtattaa cttccatcga agtttctcca gttttacctt caattgcaaa aggactaact   1260
cagaaattta cggcgatcgg gatttttacg gataactcca aaaaagatat tacaaatcaa   1320
gtcacttgga attcttcttc agcaatcgca agcgtgtcta acttagatga taataaaggt   1380
ctgggaaaag ctcacgctgt tggagacacg actattaccg ctactttagg aaaagtttca   1440
ggtaaaactt ggtttactgt agttcctgcg gttctcactt ctattcaaat caatcctgta   1500
aatccttctc ttgcaaaagg gttaactcaa aaatttacgg ctactgggat ctactctgac   1560
aactctaaca aggacattac ttcctccgtt acttggttct catccgattc ttcaatcgca   1620
acaatttcaa acgccaaaaa aaatcaagga aactcttacg gagcagctac aggagcaacg   1680
gatattaaag ccacattcgg aaaggtaagt agtccagttt ctacgttatc cgttactgct   1740
gcaaaacttg ttgaaataca aatcacaccg gccgctgctt ccaaagcaaa gggaatttcc   1800
```

```
gaaagattta aagcaaccgg tatttttaca gacaactcta attccgatat tacaaatcag   1860
gtcacttgga gttcatctaa tacagatatt gctgaaatta caaataccag aggaagcaaa   1920
ggtattacaa atacactcac tcccggatcg agtgaaatat ccgccgctct cggttcaatc   1980
aaaagttcta aagtaatatt gaaggtaact ccggcacaat tgatttccat tgcagtaaca   2040
cctacaaatc catcagttgc aaaaggtcta atacgacaat ttaaagccac cggaacatat   2100
acggatcatt ccgtacaaga cgtgactgcc ctagctacct ggtcttcttc caatcccaga   2160
aaagcaatgg ttaacaacgt tacaggttcg gttacaacag tggctaccgg aaatacaaat   2220
attaaagcaa cgatagactc catatccgga tcttccgttt tgaatgtcac tcctgcactt   2280
cttacttcta tcgagataac accgacgatt aactctatca ctcacggtct tacaaaacaa   2340
tttaaagcga ctggtatctt ttcagataaa tctactcaaa atttgactca gcttgtaact   2400
tggatttctt ccgatccctc caagatcaag atcgaaaata actccggtat agcaacagct   2460
tctgcattag gaagttcgaa tattacggcc atctacaaat ttgtccaaag ttccccaatt   2520
ccgatcacag tcactgactt aaaactgaaa agtataacta tcagtccttc ctcaagttca   2580
atagccaaag gattgaccca acaatttaaa gcgatcggaa cttttataga tggttctgaa   2640
caagaaatta cgaatcttgt gacctggtat tcctccaaat ccgatattgt tcctatcaat   2700
aattctgcgg gtaaaaaagg tttagcgacc gcactctcaa taggttcctc caacatctcc   2760
gcaatttaca attctataag cagtaataaa ataaatttta atgtaagcgc cgccacgtta   2820
gattccatta aaatcaatcc agtcaacaat aacatcgcca agggacttac ccaacaatat   2880
actgcgcttg gcgtttattc agactccacc attcaggaca tcagcgattt agttacatgg   2940
tccagttcca attctgactc gatcagcatc tccaattcga ccggaaccaa gggaaaagcg   3000
accgctttac agattggaaa gagcaaaatt accgcgactt acaattccat ttcgaaaaac   3060
ataaatctaa ctgtcagcgc agcaactctc tcttcgattt ttatatctcc taccaataca   3120
aatataaaca ccaccgtatc aaaacaattc tttgcaatgg gaacgtattc ggacggaacc   3180
aaaacggatt taacttcttc ggttacatgg tccagttcga atcaagctca agcaaaggtg   3240
agtaacgcat ctgaaacgaa aggattggtt acagggatta cttctggaaa tcctataatc   3300
acagcgacct acggctcagt gtcgggaaat acaattctca cagtaaacaa aaccgacacg   3360
atagctccga cggttcaatc ggtagtttct ttatcaccta ctaccatcca agttgtatat   3420
tcagaatcca taaacaatca ggaagccctt gatttatcca attacaaaat aattaatagt   3480
tccaattttt acggacattg ttcggataat acggacttca attccaattc tcaaaccgca   3540
gatttttctc ttagtagtat caaaggaagt aaaaatactt ttacgattac actttcacat   3600
tcacaaatct taaacaaatc atacacactt gtagtcaaca aacaaggaat tcacgatctt   3660
tcttccattc caaattcctt aagttgtcca aataactctg attttatagg aaaagaacaa   3720
ctcaaactta caagtgcagt ttgtaattcc ttaaaccaag tgatcgtttc tttttccaaa   3780
cctttatatt ctggaaagga agtaacaaaa tccgtggaat gttcaaatcc gtcccaatgt   3840
gaatccagat ataaatttgc aggtgtgtct tcattgggaa gtattacgag cgttagaatt   3900
ttagatggaa aagtatgcgg tggagcaccg gcagactcct cgaaaatatg tttaacacac   3960
tcccttcttc aatcaggtgg tcaatatacg atcatcgccg caaatgattt gaacggagac   4020
ggctttgaca acaaatcctg gggagcaatt cgagattcat tcgatcaaga aaacctacaa   4080
ccttctccga aagatagaat caactttata ggttgtggaa attcccctct caactttatg   4140
```

-continued

```
gatggcccga tcgtgtcaga tccttttgga gacggttccg atttcggctc tcttgtagat   4200
tacaacaatc aaatctatct aggaccgaat gtaaaaggaa accaagcagc tcgattcaat   4260
tacgacggaa cttttccgga atctattttc ttttctttta cccaagataa aaatgccact   4320
aaccgtgctt cttcaagaga tggaggaatt ccggttccga attacgttac gatcggtcat   4380
accggttgta ctctcaatag tgcagacatc actactggat gtggtccaga taacgaagat   4440
ggacgtgggg tttttgccac cggatcatta gacaaaaaat ctcatatttt tatagcaggt   4500
tcaaaaccaa ggagattcaa ctatctctat tattcctcag ataccgatac aaaccttaat   4560
tttaaatata tcagtatggg aaaaattact ggattggcga ctgcaggaac ttcatctatc   4620
gcagttctag acgatcggat ccatgtaggt tttgcaaaaa aaaatcaaaa tctaaacgca   4680
cctgatttcg gtaaaatcac ctttaataca tccgagcaca atcgatgtgc aattgtaaac   4740
aactgtgaag cctctgacgg ataccgcggt aatcgtttta gaatcgatag aatgccttac   4800
tttggcggcg gctccgtgga tgcagtcaat tataaaactc ataaatctga taattcctcg   4860
atcaactggg gttattatgt gggaatagat tctctattcg tttttaaaga aaaactttac   4920
gccgcaaacg gaggatttcc aaattcatta cataatggaa gtataataca ctctaccagt   4980
gcaaatccta gtccttgtga aggaatcaat cgttgttcca gttggaaaga cacagcacct   5040
agatccaatc cgaagtggca taactctcct cataccaatt ggttttcact ggagcttaca   5100
aagtatcgag atttaattcc ggcggataaa gcattctctc aattcgcaga atttaacgga   5160
agattgtatg taacaagaac gatctgtgta acgaaagaag atcactccgg actcagacaa   5220
agtttacaaa ctttgaaagg ttgtacagac ggaagttata caaatcgaag acctcaactt   5280
tggaaatgtg atccgactct aaccggcgat acaacaacct gcgaagcaaa agattggtct   5340
ttagtaggag ataatggaac cgggtttacg aatttcggag acgattccaa tcacagtatg   5400
acgatggtag ttgcaagtgg atcttatctc tacgtaggtt ttgacaacga aaacggaatt   5460
caaatctgga gaacaaatct tgaaaatcct ggaagttcat cacacgactg ggagcctata   5520
ggaataggcg gattaagaga cgttaccaat cgtcaaattt attcggctat atccggaatg   5580
aattttggtg taaatttcgt atatataagc gtaggaaata aagatcaacc ggttaaaatt   5640
tacagacaac agaaccaa                                                 5658
```

<210> SEQ ID NO 6
<211> LENGTH: 1886
<212> TYPE: PRT
<213> ORGANISM: Leptospira kirschneri

<400> SEQUENCE: 6

```
Met Lys Arg Thr Phe Cys Ile Ser Ile Leu Leu Ser Met Phe Phe Gln
1               5                   10                  15

Ser Cys Met Ser Trp Pro Leu Leu Thr Ser Leu Ala Gly Leu Ala Ala
            20                  25                  30

Gly Lys Lys Ser Asn Gly Leu Pro Phe Phe His Leu Leu Leu Ser Asn
        35                  40                  45

Ser Asp Pro Val Ile Thr Arg Ile Glu Leu Ser Tyr Gln Asn Ser Ser
    50                  55                  60

Ile Ala Lys Gly Thr Ser Thr Thr Leu Glu Val Thr Ala Ile Phe Asp
65                  70                  75                  80

Asn Gly Thr Asn Gln Asn Ile Thr Asp Ser Thr Ser Ile Val Ser Asp
                85                  90                  95

Ala Gln Ser Ile Val Asp Ile Gln Gly Asn Arg Val Arg Gly Ile Ala
```

-continued

```
            100                 105                 110

Ser Gly Ser Ser Ile Ile Lys Ala Glu Tyr Asn Gly Met Tyr Ser Glu
        115                 120                 125

Gln Lys Ile Thr Val Thr Pro Ala Thr Ile Asn Ser Ile Gln Val Thr
    130                 135                 140

Ser Leu Asp Asp Gly Ile Leu Pro Lys Gly Thr Asn Arg Gln Phe Ala
145                 150                 155                 160

Ala Ile Gly Ile Phe Ser Asp Gly Ser His Gln Asp Ile Ser Asn Asp
                165                 170                 175

Pro Leu Ile Val Trp Ser Ser Ser Asn Ile Asp Leu Val Arg Val Asp
            180                 185                 190

Asp Ser Gly Leu Ala Ser Gly Ile Asn Leu Gly Thr Ala His Ile Arg
        195                 200                 205

Ala Ser Phe Gln Ser Lys Gln Ala Ser Glu Glu Ile Thr Val Gly Asp
    210                 215                 220

Ala Val Leu Ser Ser Ile Gln Val Thr Ser Asn Ser Pro Asn Ile Pro
225                 230                 235                 240

Leu Gly Lys Lys Gln Lys Leu Thr Ala Thr Gly Ile Tyr Ser Asp Asn
                245                 250                 255

Ser Asn Arg Asp Ile Ser Ser Ser Val Ile Trp Asn Ser Ser Asn Ser
            260                 265                 270

Thr Ile Ala Asn Ile Gln Asn Asn Gly Ile Leu Glu Thr Ala Asp Thr
        275                 280                 285

Gly Ile Val Thr Val Ser Ala Ser Arg Gly Asn Ile Asn Gly Ser Ile
    290                 295                 300

Lys Leu Ile Val Thr Pro Ala Ala Leu Val Ser Ile Ser Val Ser Pro
305                 310                 315                 320

Thr Asn Ser Ala Val Ala Lys Gly Leu Gln Glu Asn Phe Lys Ala Thr
                325                 330                 335

Gly Ile Phe Thr Asp Asn Ser Asn Ser Asp Ile Thr Asp Gln Val Thr
            340                 345                 350

Trp Asp Ser Ser Asn Pro Asp Ile Leu Ser Ile Ser Asn Ala Ser Asp
        355                 360                 365

Ser His Gly Leu Ala Ser Thr Leu Asn Gln Gly Asn Val Lys Val Thr
    370                 375                 380

Ala Ser Ile Gly Gly Ile Gln Gly Ser Thr Asp Phe Lys Val Thr Gln
385                 390                 395                 400

Glu Val Leu Thr Ser Ile Glu Val Ser Pro Val Leu Pro Ser Ile Ala
                405                 410                 415

Lys Gly Leu Thr Gln Lys Phe Thr Ala Ile Gly Ile Phe Thr Asp Asn
            420                 425                 430

Ser Lys Lys Asp Ile Thr Asn Gln Val Thr Trp Asn Ser Ser Ser Ala
        435                 440                 445

Ile Ala Ser Val Ser Asn Leu Asp Asp Asn Lys Gly Leu Gly Lys Ala
    450                 455                 460

His Ala Val Gly Asp Thr Thr Ile Thr Ala Thr Leu Gly Lys Val Ser
465                 470                 475                 480

Gly Lys Thr Trp Phe Thr Val Val Pro Ala Val Leu Thr Ser Ile Gln
                485                 490                 495

Ile Asn Pro Val Asn Pro Ser Leu Ala Lys Gly Leu Thr Gln Lys Phe
            500                 505                 510

Thr Ala Thr Gly Ile Tyr Ser Asp Asn Ser Asn Lys Asp Ile Thr Ser
        515                 520                 525
```

-continued

```
Ser Val Thr Trp Phe Ser Ser Asp Ser Ser Ile Ala Thr Ile Ser Asn
    530                 535                 540

Ala Lys Lys Asn Gln Gly Asn Ser Tyr Gly Ala Ala Thr Gly Ala Thr
545                 550                 555                 560

Asp Ile Lys Ala Thr Phe Gly Lys Val Ser Ser Pro Val Ser Thr Leu
                565                 570                 575

Ser Val Thr Ala Ala Lys Leu Val Glu Ile Gln Ile Thr Pro Ala Ala
            580                 585                 590

Ala Ser Lys Ala Lys Gly Ile Ser Glu Arg Phe Lys Ala Thr Gly Ile
        595                 600                 605

Phe Thr Asp Asn Ser Asn Ser Asp Ile Thr Asn Gln Val Thr Trp Ser
    610                 615                 620

Ser Ser Asn Thr Asp Ile Ala Glu Ile Thr Asn Thr Arg Gly Ser Lys
625                 630                 635                 640

Gly Ile Thr Asn Thr Leu Thr Pro Gly Ser Ser Glu Ile Ser Ala Ala
                645                 650                 655

Leu Gly Ser Ile Lys Ser Ser Lys Val Ile Leu Lys Val Thr Pro Ala
            660                 665                 670

Gln Leu Ile Ser Ile Ala Val Thr Pro Thr Asn Pro Ser Val Ala Lys
        675                 680                 685

Gly Leu Ile Arg Gln Phe Lys Ala Thr Gly Thr Tyr Thr Asp His Ser
    690                 695                 700

Val Gln Asp Val Thr Ala Leu Ala Thr Trp Ser Ser Ser Asn Pro Arg
705                 710                 715                 720

Lys Ala Met Val Asn Asn Val Thr Gly Ser Val Thr Thr Val Ala Thr
                725                 730                 735

Gly Asn Thr Asn Ile Lys Ala Thr Ile Asp Ser Ile Ser Gly Ser Ser
            740                 745                 750

Val Leu Asn Val Thr Pro Ala Leu Leu Thr Ser Ile Glu Ile Thr Pro
        755                 760                 765

Thr Ile Asn Ser Ile Thr His Gly Leu Thr Lys Gln Phe Lys Ala Thr
    770                 775                 780

Gly Ile Phe Ser Asp Lys Ser Thr Gln Asn Leu Thr Gln Leu Val Thr
785                 790                 795                 800

Trp Ile Ser Ser Asp Pro Ser Lys Ile Lys Ile Glu Asn Asn Ser Gly
                805                 810                 815

Ile Ala Thr Ala Ser Ala Leu Gly Ser Ser Asn Ile Thr Ala Ile Tyr
            820                 825                 830

Lys Phe Val Gln Ser Ser Pro Ile Pro Ile Thr Val Thr Asp Leu Lys
        835                 840                 845

Leu Lys Ser Ile Thr Ile Ser Pro Ser Ser Ser Ser Ile Ala Lys Gly
    850                 855                 860

Leu Thr Gln Gln Phe Lys Ala Ile Gly Thr Phe Ile Asp Gly Ser Glu
865                 870                 875                 880

Gln Glu Ile Thr Asn Leu Val Thr Trp Tyr Ser Ser Lys Ser Asp Ile
                885                 890                 895

Val Pro Ile Asn Asn Ser Ala Gly Lys Lys Gly Leu Ala Thr Ala Leu
            900                 905                 910

Ser Ile Gly Ser Ser Asn Ile Ser Ala Ile Tyr Asn Ser Ile Ser Ser
        915                 920                 925

Asn Lys Ile Asn Phe Asn Val Ser Ala Ala Thr Leu Asp Ser Ile Lys
    930                 935                 940
```

-continued

```
Ile Asn Pro Val Asn Asn Asn Ile Ala Lys Gly Leu Thr Gln Gln Tyr
945                 950                 955                 960

Thr Ala Leu Gly Val Tyr Ser Asp Ser Thr Ile Gln Asp Ile Ser Asp
                965                 970                 975

Leu Val Thr Trp Ser Ser Ser Asn Ser Asp Ser Ile Ser Ile Ser Asn
            980                 985                 990

Ser Thr Gly Thr Lys Gly Lys Ala  Thr Ala Leu Gln Ile  Gly Lys Ser
        995                 1000                 1005

Lys Ile  Thr Ala Thr Tyr Asn  Ser Ile Ser Lys Asn  Ile Asn Leu
    1010                 1015                 1020

Thr Val  Ser Ala Ala Thr Leu  Ser Ser Ile Phe Ile  Ser Pro Thr
    1025                 1030                 1035

Asn Thr  Asn Ile Asn Thr Thr  Val Ser Lys Gln Phe  Phe Ala Met
    1040                 1045                 1050

Gly Thr  Tyr Ser Asp Gly Thr  Lys Thr Asp Leu Thr  Ser Ser Val
    1055                 1060                 1065

Thr Trp  Ser Ser Ser Asn Gln  Ala Gln Ala Lys Val  Ser Asn Ala
    1070                 1075                 1080

Ser Glu  Thr Lys Gly Leu Val  Thr Gly Ile Thr Ser  Gly Asn Pro
    1085                 1090                 1095

Ile Ile  Thr Ala Thr Tyr Gly  Ser Val Ser Gly Asn  Thr Ile Leu
    1100                 1105                 1110

Thr Val  Asn Lys Thr Asp Thr  Ile Ala Pro Thr Val  Gln Ser Val
    1115                 1120                 1125

Val Ser  Leu Ser Pro Thr Thr  Ile Gln Val Val Tyr  Ser Glu Ser
    1130                 1135                 1140

Ile Asn  Asn Gln Glu Ala Leu  Asp Leu Ser Asn Tyr  Lys Ile Ile
    1145                 1150                 1155

Asn Ser  Ser Asn Phe Tyr Gly  His Cys Ser Asp Asn  Thr Asp Phe
    1160                 1165                 1170

Asn Ser  Asn Ser Gln Thr Ala  Asp Phe Ser Leu Ser  Ser Ile Lys
    1175                 1180                 1185

Gly Ser  Lys Asn Thr Phe Thr  Ile Thr Leu Ser His  Ser Gln Ile
    1190                 1195                 1200

Leu Asn  Lys Ser Tyr Thr Leu  Val Val Asn Lys Gln  Gly Ile His
    1205                 1210                 1215

Asp Leu  Ser Ser Ile Pro Asn  Ser Leu Ser Cys Pro  Asn Asn Ser
    1220                 1225                 1230

Asp Phe  Ile Gly Lys Glu Gln  Leu Lys Leu Thr Ser  Ala Val Cys
    1235                 1240                 1245

Asn Ser  Leu Asn Gln Val Ile  Val Ser Phe Ser Lys  Pro Leu Tyr
    1250                 1255                 1260

Ser Gly  Lys Glu Val Thr Lys  Ser Val Glu Cys Ser  Asn Pro Ser
    1265                 1270                 1275

Gln Cys  Glu Ser Arg Tyr Lys  Phe Ala Gly Val Ser  Ser Leu Gly
    1280                 1285                 1290

Ser Ile  Thr Ser Val Arg Ile  Leu Asp Gly Lys Val  Cys Gly Gly
    1295                 1300                 1305

Ala Pro  Ala Asp Ser Ser Lys  Ile Cys Leu Thr His  Ser Leu Leu
    1310                 1315                 1320

Gln Ser  Gly Gly Gln Tyr Thr  Ile Ile Ala Ala Asn  Asp Leu Asn
    1325                 1330                 1335

Gly Asp  Gly Phe Asp Asn Lys  Ser Trp Gly Ala Ile  Arg Asp Ser
```

-continued

```
    1340                1345                1350

Phe Asp  Gln Glu Asn Leu Gln  Pro Ser Pro Lys Asp  Arg Ile Asn
    1355                1360                1365

Phe Ile  Gly Cys Gly Asn Ser  Pro Leu Asn Phe Met  Asp Gly Pro
    1370                1375                1380

Ile Val  Ser Asp Pro Phe Gly  Asp Gly Ser Asp Phe  Gly Ser Leu
    1385                1390                1395

Val Asp  Tyr Asn Asn Gln Ile  Tyr Leu Gly Pro Asn  Val Lys Gly
    1400                1405                1410

Asn Gln  Ala Ala Arg Phe Asn  Tyr Asp Gly Thr Phe  Pro Glu Ser
    1415                1420                1425

Ile Phe  Phe Ser Phe Thr Gln  Asp Lys Asn Ala Thr  Asn Arg Ala
    1430                1435                1440

Ser Ser  Arg Asp Gly Gly Ile  Pro Val Pro Asn Tyr  Val Thr Ile
    1445                1450                1455

Gly His  Thr Gly Cys Thr Leu  Asn Ser Ala Asp Ile  Thr Thr Gly
    1460                1465                1470

Cys Gly  Pro Asp Asn Glu Asp  Gly Arg Gly Val Phe  Ala Thr Gly
    1475                1480                1485

Ser Leu  Asp Lys Lys Ser His  Ile Phe Ile Ala Gly  Ser Lys Pro
    1490                1495                1500

Arg Arg  Phe Asn Tyr Leu Tyr  Tyr Ser Ser Asp Thr  Asp Thr Asn
    1505                1510                1515

Leu Asn  Phe Lys Tyr Ile Ser  Met Gly Lys Ile Thr  Gly Leu Ala
    1520                1525                1530

Thr Ala  Gly Thr Ser Ser Ile  Ala Val Leu Asp Asp  Arg Ile His
    1535                1540                1545

Val Gly  Phe Ala Lys Lys Asn  Gln Asn Leu Asn Ala  Pro Asp Phe
    1550                1555                1560

Gly Lys  Ile Thr Phe Asn Thr  Ser Glu His Asn Arg  Cys Ala Ile
    1565                1570                1575

Val Asn  Asn Cys Glu Ala Ser  Asp Gly Tyr Arg Gly  Asn Arg Phe
    1580                1585                1590

Arg Ile  Asp Arg Met Pro Tyr  Phe Gly Gly Gly Ser  Val Asp Ala
    1595                1600                1605

Val Asn  Tyr Lys Thr His Lys  Ser Asp Asn Ser Ser  Ile Asn Trp
    1610                1615                1620

Gly Tyr  Tyr Val Gly Ile Asp  Ser Leu Phe Val Phe  Lys Glu Lys
    1625                1630                1635

Leu Tyr  Ala Ala Asn Gly Gly  Phe Pro Asn Ser Leu  His Asn Gly
    1640                1645                1650

Ser Ile  Ile His Ser Thr Ser  Ala Asn Pro Ser Pro  Cys Glu Gly
    1655                1660                1665

Ile Asn  Arg Cys Ser Ser Trp  Lys Asp Thr Ala Pro  Arg Ser Asn
    1670                1675                1680

Pro Lys  Trp His Asn Ser Pro  His Thr Asn Trp Phe  Ser Leu Glu
    1685                1690                1695

Leu Thr  Lys Tyr Arg Asp Leu  Ile Pro Ala Asp Lys  Ala Phe Ser
    1700                1705                1710

Gln Phe  Ala Glu Phe Asn Gly  Arg Leu Tyr Val Thr  Arg Thr Ile
    1715                1720                1725

Cys Val  Thr Lys Glu Asp His  Ser Gly Leu Arg Gln  Ser Leu Gln
    1730                1735                1740
```

-continued

Thr Leu Lys Gly Cys Thr Asp Gly Ser Tyr Thr Asn Arg Arg Pro
1745 1750 1755

Gln Leu Trp Lys Cys Asp Pro Thr Leu Thr Gly Asp Thr Thr Thr
1760 1765 1770

Cys Glu Ala Lys Asp Trp Ser Leu Val Gly Asp Asn Gly Thr Gly
1775 1780 1785

Phe Thr Asn Phe Gly Asp Asp Ser Asn His Ser Met Thr Met Val
1790 1795 1800

Val Ala Ser Gly Ser Tyr Leu Tyr Val Gly Phe Asp Asn Glu Asn
1805 1810 1815

Gly Ile Gln Ile Trp Arg Thr Asn Leu Glu Asn Pro Gly Ser Ser
1820 1825 1830

Ser His Asp Trp Glu Pro Ile Gly Ile Gly Gly Leu Arg Asp Val
1835 1840 1845

Thr Asn Arg Gln Ile Tyr Ser Ala Ile Ser Gly Met Asn Phe Gly
1850 1855 1860

Val Asn Phe Val Tyr Ile Ser Val Gly Asn Lys Asp Gln Pro Val
1865 1870 1875

Lys Ile Tyr Arg Gln Gln Asn Gln
1880 1885

<210> SEQ ID NO 7
<211> LENGTH: 1557
<212> TYPE: DNA
<213> ORGANISM: Leptospira interrogans

<400> SEQUENCE: 7
attaccgtta caccagccat tcttaactca attcaagtta cgagtttaga gtcaggtata 60
ctacctaaag gtactaatcg tcaattctca gccatcggta tcttttcgga tggttctcat 120
caggatattt ccaacgaacc actgatcgtt tggtcttcca gtaatcctga tttggttcga 180
gtagatgatt cagggttggc atcagggatc aatttaggaa cagctcatat tcgtgcatcc 240
tttcaatcaa aacaaggggc tgaagaaatg accgttggag atgctgttct ctctcaaatc 300
caagtaactt caaacgatct gaatattcct ctcggaaaaa aacaaaaact aacagctacg 360
ggaatctatt cggataactc taacagggat atttcctctt ctgttatttg gaattcttct 420
aattccacta tcgctaatat tcaaaacaac ggaatattag aaacagctga tactggtatt 480
gtcactgttt ctgcttctag cgagaatata atcggatccg taaaactaat cgttactcca 540
gcagccttag tttctatttc tgtttctccg acaaattcta cagttgcaaa aggtttacaa 600
gaaaacttta aagctacagg gatctttaca gataattcaa actcggatat taccgaccaa 660
gttacttggg attcttctaa taccgatatt ctctcaattt ccaatgcaag tgatagccac 720
ggattagctt ccacactcaa ccaagggaat gttaaagtca ctgcttccat cggtggaata 780
caaggatcca ctgattttaa agttacacaa gctgcattga cttccatcga agtctctcca 840
actcgcactt ccattgcaaa aggactaact caaaagttta ctgcgatcgg gatttttacg 900
gataactcta agaaggatat tacggatcaa gtcacttgga attcttcttc agcaatcgta 960
agcgtgtcta acttagacaa caataaaggt ctgggaaaaa ccaactcagt tggaaacacg 1020
actattaccg caaccttagg aaaagtttca ggtaacactt ggtttactgt agttcctgcg 1080
gttctcactt ctattcaaat caatcctgta aatccttctc ttgcaaaagg gttaactcaa 1140
aaatttacgg ctactgggat ctactctgac aactctaaca aggacattac ttccgctgtt 1200

-continued

```
acgtggttct catccgattc ttcaatcgcg acgatttcaa acgcccaaaa aaatcaagga   1260

aacgcttacg gagcagctac aggagcaacg gatattaaag ccacattcgg aaaggtaagt   1320

agtccggttt ctacgttatc tgttacagct gcaaagcttg ttgaaatcca aatcacaccg   1380

gctgctgctt ccaaagcaaa gggactcaca gaaagattca aggctactgg tatctttacg   1440

gataactcaa attccgatat tacaaatcaa gttacctgga attcctctaa tacggatatt   1500

gctgaaatta aaaataccag tggaagtaaa ggtattacaa atacactcac tccagga      1557


<210> SEQ ID NO 8
<211> LENGTH: 519
<212> TYPE: PRT
<213> ORGANISM: Leptospira interrogans

<400> SEQUENCE: 8

Ile Thr Val Thr Pro Ala Ile Leu Asn Ser Ile Gln Val Thr Ser Leu
1               5                   10                  15

Glu Ser Gly Ile Leu Pro Lys Gly Thr Asn Arg Gln Phe Ser Ala Ile
            20                  25                  30

Gly Ile Phe Ser Asp Gly Ser His Gln Asp Ile Ser Asn Glu Pro Leu
        35                  40                  45

Ile Val Trp Ser Ser Ser Asn Pro Asp Leu Val Arg Val Asp Asp Ser
    50                  55                  60

Gly Leu Ala Ser Gly Ile Asn Leu Gly Thr Ala His Ile Arg Ala Ser
65                  70                  75                  80

Phe Gln Ser Lys Gln Gly Ala Glu Glu Met Thr Val Gly Asp Ala Val
                85                  90                  95

Leu Ser Gln Ile Gln Val Thr Ser Asn Asp Leu Asn Ile Pro Leu Gly
            100                 105                 110

Lys Lys Gln Lys Leu Thr Ala Thr Gly Ile Tyr Ser Asp Asn Ser Asn
        115                 120                 125

Arg Asp Ile Ser Ser Ser Val Ile Trp Asn Ser Ser Asn Ser Thr Ile
    130                 135                 140

Ala Asn Ile Gln Asn Asn Gly Ile Leu Glu Thr Ala Asp Thr Gly Ile
145                 150                 155                 160

Val Thr Val Ser Ala Ser Ser Glu Asn Ile Ile Gly Ser Val Lys Leu
                165                 170                 175

Ile Val Thr Pro Ala Ala Leu Val Ser Ile Ser Val Ser Pro Thr Asn
            180                 185                 190

Ser Thr Val Ala Lys Gly Leu Gln Glu Asn Phe Lys Ala Thr Gly Ile
        195                 200                 205

Phe Thr Asp Asn Ser Asn Ser Asp Ile Thr Asp Gln Val Thr Trp Asp
    210                 215                 220

Ser Ser Asn Thr Asp Ile Leu Ser Ile Ser Asn Ala Ser Asp Ser His
225                 230                 235                 240

Gly Leu Ala Ser Thr Leu Asn Gln Gly Asn Val Lys Val Thr Ala Ser
                245                 250                 255

Ile Gly Gly Ile Gln Gly Ser Thr Asp Phe Lys Val Thr Gln Ala Ala
            260                 265                 270

Leu Thr Ser Ile Glu Val Ser Pro Thr Arg Thr Ser Ile Ala Lys Gly
        275                 280                 285

Leu Thr Gln Lys Phe Thr Ala Ile Gly Ile Phe Thr Asp Asn Ser Lys
    290                 295                 300

Lys Asp Ile Thr Asp Gln Val Thr Trp Asn Ser Ser Ser Ala Ile Val
305                 310                 315                 320
```

```
Ser Val Ser Asn Leu Asp Asn Asn Lys Gly Leu Gly Lys Thr Asn Ser
                325                 330                 335

Val Gly Asn Thr Thr Ile Thr Ala Thr Leu Gly Lys Val Ser Gly Asn
            340                 345                 350

Thr Trp Phe Thr Val Val Pro Ala Val Leu Thr Ser Ile Gln Ile Asn
        355                 360                 365

Pro Val Asn Pro Ser Leu Ala Lys Gly Leu Thr Gln Lys Phe Thr Ala
    370                 375                 380

Thr Gly Ile Tyr Ser Asp Asn Ser Asn Lys Asp Ile Thr Ser Ala Val
385                 390                 395                 400

Thr Trp Phe Ser Ser Asp Ser Ser Ile Ala Thr Ile Ser Asn Ala Gln
                405                 410                 415

Lys Asn Gln Gly Asn Ala Tyr Gly Ala Ala Thr Gly Ala Thr Asp Ile
            420                 425                 430

Lys Ala Thr Phe Gly Lys Val Ser Ser Pro Val Ser Thr Leu Ser Val
        435                 440                 445

Thr Ala Ala Lys Leu Val Glu Ile Gln Ile Thr Pro Ala Ala Ala Ser
    450                 455                 460

Lys Ala Lys Gly Leu Thr Glu Arg Phe Lys Ala Thr Gly Ile Phe Thr
465                 470                 475                 480

Asp Asn Ser Asn Ser Asp Ile Thr Asn Gln Val Thr Trp Asn Ser Ser
                485                 490                 495

Asn Thr Asp Ile Ala Glu Ile Lys Asn Thr Ser Gly Ser Lys Gly Ile
            500                 505                 510

Thr Asn Thr Leu Thr Pro Gly
        515


<210> SEQ ID NO 9
<211> LENGTH: 600
<212> TYPE: DNA
<213> ORGANISM: Leptospira interrogans

<400> SEQUENCE: 9

cataactctc ctcataacaa ttggttttca ctggagctta caaagtatcg gaatttaatt     60

ccggcggata aagcattctc tcaattcgca gaatttaacg gaagattgta tgtaacaaga    120

acgatctgcg taacgaaaga agatcactcc ggactcagac aaagtttaca aactgtggaa    180

ggttgtacgg acggaagtta tacaaatcga agaccccaac tttggaaatg tgatccgact    240

ctaaccggcg atacaacaac ctgcgaagca gaagattggt ctttagtagg agataacgga    300

accggattta caaactttgg agacaattcc aatcacagta tgacgatgat ggttgcaagt    360

ggatcttatc tctacatagg ttttgataac gaaaacggaa ttcaaatctg gagaacaaat    420

cttgaaaatc ctggaagttc atcacacaac tgggaaccta taggaatagg cggattaaga    480

gacgttacca atcgtcaaat ttattcggct atatccggaa tgaattttgg tgtaaatttc    540

gtatatataa gcgtaggaaa caaaaataaa ccggtcaaaa tttacagaca acagaatcaa    600


<210> SEQ ID NO 10
<211> LENGTH: 200
<212> TYPE: PRT
<213> ORGANISM: Leptospira interrogans

<400> SEQUENCE: 10

His Asn Ser Pro His Asn Asn Trp Phe Ser Leu Glu Leu Thr Lys Tyr
1               5                   10                  15
```

```
Arg Asn Leu Ile Pro Ala Asp Lys Ala Phe Ser Gln Phe Ala Glu Phe
            20                  25                  30

Asn Gly Arg Leu Tyr Val Thr Arg Thr Ile Cys Val Thr Lys Glu Asp
        35                  40                  45

His Ser Gly Leu Arg Gln Ser Leu Gln Thr Val Glu Gly Cys Thr Asp
    50                  55                  60

Gly Ser Tyr Thr Asn Arg Arg Pro Gln Leu Trp Lys Cys Asp Pro Thr
65                  70                  75                  80

Leu Thr Gly Asp Thr Thr Thr Cys Glu Ala Glu Asp Trp Ser Leu Val
                85                  90                  95

Gly Asp Asn Gly Thr Gly Phe Thr Asn Phe Gly Asp Asn Ser Asn His
            100                 105                 110

Ser Met Thr Met Met Val Ala Ser Gly Ser Tyr Leu Tyr Ile Gly Phe
        115                 120                 125

Asp Asn Glu Asn Gly Ile Gln Ile Trp Arg Thr Asn Leu Glu Asn Pro
    130                 135                 140

Gly Ser Ser Ser His Asn Trp Glu Pro Ile Gly Ile Gly Gly Leu Arg
145                 150                 155                 160

Asp Val Thr Asn Arg Gln Ile Tyr Ser Ala Ile Ser Gly Met Asn Phe
                165                 170                 175

Gly Val Asn Phe Val Tyr Ile Ser Val Gly Asn Lys Asn Lys Pro Val
            180                 185                 190

Lys Ile Tyr Arg Gln Gln Asn Gln
        195                 200


<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11

gattttaaag ttacacaagc                                                20


<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12

aaaccggact acttaccttt cc                                             22


<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13

ttacggctac aggtattttt acg                                            23


<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide
```

-continued

<400> SEQUENCE: 14
attggaagat ttccaagtaa cc 22

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
tatctacgct gcaaatgg 18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
ttgttggcga tacgtccg 18

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
cataactctc ctcataaca 19

<210> SEQ ID NO 18
<211> LENGTH: 18
<212> TYPE: DNA
<213> ORGANISM: Artificial Sequence
<220> FEATURE:
<223> OTHER INFORMATION: Syntehtic oligonucleotide

<400> SEQUENCE: 18
tatgtagaga taagatcc 18

<210> SEQ ID NO 19
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 19
cgcagaaatt ttagaggaac ctacag 26

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 20
tttgactcca agacgcagag gatgat 26

-continued

<210> SEQ ID NO 21
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 21
attttcaaga tttgttctcc agattt 26

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
attacttctt gaacatctgc ttgat 25

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 23
ctgctacgct tgttgacata gaagta 26

<210> SEQ ID NO 24
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 24
tagaaccaac acgaaatggc acaaca 26

<210> SEQ ID NO 25
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 25
atccgaagtg gcataactct cctcat 26

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
tgaaaagaac attaccagcg ttgta 25

<210> SEQ ID NO 27
<211> LENGTH: 33
<212> TYPE: DNA
<213> ORGANISM: Artificial Sequence
<220> FEATURE:
<223> OTHER INFORMATION: Synthetic oligonucleotide -continued

<400> SEQUENCE: 27
atgggactcg agattaccgt tacaccagcc att 33

<210> SEQ ID NO 28
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 28
attccatggt tatcctggag tgagtgtatt tgt 33

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 29
aacctcgagc ataactctcc tcataac 27

<210> SEQ ID NO 30
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 30
ttcgaattct tattgattct gttgtctg 28

PROTEINS WITH REPETITIVE BACTERIAL-IG-LIKE (BIG) DOMAINS PRESENT IN *LEPTOSPIRA* SPECIES

CROSS REFERENCE TO RELATED APPLICATIONS

This is a divisional of U.S. application Ser. No. 14/281,580, filed May 19, 2014 now U.S. Pat. No. 9,133,250 issued Sep. 15, 2015; which is a divisional of U.S. application Ser. No. 13/869,660, filed Apr. 24, 2013, now U.S. Pat. No. 8,802,835, issued Aug. 12, 2014; which is a divisional of U.S. application Ser. No. 13/525,157, filed Jun. 15, 2012, now U.S. Pat. No. 8,445,658, issued May 21, 2013; which is a divisional of U.S. application Ser. No. 13/359,354, filed Jan. 26, 2012, now U.S. Pat. No. 8,216,594, issued Jul. 10, 2012; which is a divisional of U.S. application Ser. No. 13/216,214, filed Aug. 23, 2011, now U.S. Pat. No. 8,124,110, issued Feb. 28, 2012; which is a divisional of U.S. application Ser. No. 13/078,879, filed Apr. 1, 2011, now U.S. Pat. No. 8,021,673, issued Sep. 20, 2011; which is a divisional of U.S. application Ser. No. 12/728,177, filed Mar. 19, 2010, now U.S. Pat. No. 7,935,357, issued May 3, 2011; which is a divisional of application Ser. No. 11/332,464, filed Jan. 17, 2006, now U.S. Pat. No. 7,718,183, issued May 18, 2010; which is a divisional of U.S. application Ser. No. 11/005,565, filed Dec. 7, 2004 (abandoned); which is a divisional of U.S. application Ser. No. 10/147,299, filed May 17, 2002 (abandoned). The entire contents of each of the earlier applications is hereby incorporated by reference.

ACKNOWLEDGEMENT OF GOVERNMENT SUPPORT

This invention was made with Government support under Grant Nos. AI001605, AI034431, HL051967, and TW000905 awarded by the National Institutes of Health. The Government has certain rights in this invention.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Aug. 4, 2015, and having a size of 78,665 bytes, as permitted under 37 CFR 1.821(c). The material in the aforementioned file is hereby incorporated by reference in its entirety.

FIELD

The invention relates to three isolated DNA molecules that encode for proteins, BigL1, BigL2 and BigL3, in the *Leptospira* sp bacterium which have repetitive Bacterial-Ig-like (Big) domains and their use in diagnostic, therapeutic and vaccine applications. According to the present invention, the isolated molecules encoding for BigL1, BigL2 and BigL3 proteins are used for the diagnosis and prevention of infection with *Leptospira* species that are capable of producing disease in humans and other mammals, including those of veterinary importance.

BACKGROUND

Spirochetes are motile, helically shaped bacteria and include three genera, *Leptospira, Borrelia* and *Treponema*, which are pathogens of humans and other animals. *Borrelia* and *Treponema* are the causative agents of diseases that include Lyme disease, relapsing fever, syphilis and yaws. *Leptospira* consists of a genetically diverse group of eight pathogenic and four non-pathogenic, saprophytic species (1, 2). Leptospires are also classified according to serovar status—more than 200 pathogenic serovars have been identified. Structural heterogeneity in lipopolysaccharide moieties appears to be the basis for the large degree of antigenic variation observed among serovars (1, 2).

Leptospirosis is a zoonotic disease: transmission to humans occurs through contact with domestic or wild animal reservoirs or an environment contaminated by their urine. Infection produces a wide spectrum of clinical manifestations. The early-phase of illness is characterized by fever, chills, headache and severe myalgias. Disease progresses in 5 to 15% of the clinical infections to produce severe multisystem complications such as jaundice, renal insufficiency and hemorrhagic manifestations (1-4). Severe leptospirosis is associated with mortality rates of 5-40%.

Leptospirosis has a world-wide distribution. Because of the large spectrum of animal species that serve as reservoirs, it is considered to be the most widespread zoonotic disease (1). Leptospirosis is traditionally an important occupational disease among risk groups such as military personnel, farmers, miners, sewage and refuse removal workers, veterinarians and abattoir workers (1-3). However, new patterns of disease transmission have emerged recently that emphasize the growing importance of leptospirosis as a public health problem. In developed countries, leptospirosis has become the cause of outbreaks associated with recreational activities (1) and sporting events (1, 4, 5). In Brazil and other developing countries, underlying conditions of poverty have produced large urban epidemics of leptospirosis associated with high mortality (4, 5).

In addition to its public health impact, leptospirosis is a major economic burden as the cause of disease in livestock and domestic animals (2). Leptospirosis produces abortions, stillbirths, infertility, failure to thrive, reduced milk production and death in animals such as cows, pigs, sheep, goats, horses and dogs and induces chronic infection and shedding of pathogenic leptospires in livestock (2) and therefore represents an additional source of economic loss for the animal husbandry industry because of current international and national quarantine regulations.

The control of human and animal leptospirosis is hindered by the current lack of adequate diagnostic tools. The standard serologic test, the microscopic agglutination test (MAT), is inadequate for rapid case identification since it can only be performed in few reference laboratories and requires analyses of paired sera to achieve sufficient sensitivity (1, 2). Dependence upon the MAT results in delays in establishing the cause of outbreaks as seen in several investigations (1, 2). Enzyme-linked immunosorbent assays (ELISA), and other rapid serologic tests based on whole-cell leptospiral antigen preparations have been developed for use as an alternative method to screen for leptospiral infection, although the MAT is still required for case confirmation (1, 2). Recombinant antigen-based serologic tests are widely used in screening for spirochetal infections such as Lyme disease and syphilis, but the use of recombinant proteins for serodiagnosis of leptospirosis has not been widely investigated. Recently, a recombinant flagellar-antigen immuno-capture assay was described for serodiagnosis of bovine leptospirosis (6). A recombinant heat shock protein, Hsp58, showed a high degree of ELISA reactivity with serum samples from a small number of human cases (7). However, the utility of recombinant antigens for the serodiagnosis of leptospirosis has not been investigated in large validation studies.

Furthermore, there are no effective interventions presently available, which control or prevent leptospirosis. Environmental control measures are difficult to implement because of the long-term survival of pathogenic leptospires in soil and water and the abundance of wild and domestic animal reservoirs (1, 3). Efforts have focused on developing protective immunization as an intervention against leptospirosis. Currently-available vaccines are based on inactivated whole cell or membrane preparations of pathogenic leptospires and appear to induce protective responses through induction of antibodies against leptospiral lipopolysaccharide (1, 3). However, these vaccines do not induce long-term protection against infection. Furthermore, they do not provide cross-protective immunity against leptospiral serovars that are not included in the vaccine preparation. The large number of pathogenic serovars (>200) and the cost of producing a multi-serovar vaccine have been major limitations in developing efficacious vaccines through strategies based on whole cell or membrane preparations.

The mechanism of pathogenesis in leptospirosis, as in spirochetal disease such as Lyme disease and syphilis, relies on the pathogen's ability to widely disseminate within the host during the early stage of infection (2). Membrane-associated leptospiral proteins are presumed to mediate interactions that enable entry and dissemination through host tissues. Putative surface-associated virulence factors serve as candidates for vaccine strategies that induce responses to these factors which block dissemination in the host. Furthermore, membrane-associated proteins would be accessible to the immune response during host infection and therefore, constitute targets for immune protection through mechanisms such as antibody-dependent phagocytosis and complement-mediated killing. Production of these antigen targets as recombinant proteins offers a cost-effective approach for protective immunization for leptospirosis as a sub-unit based vaccine. In addition, selection of surface-associated targets that are conserved among pathogenic leptospires can avoid the limitations encountered with currently available whole-cell vaccine preparations.

A major limitation in the field of leptospirosis has been identifying surface-associated and host-expressed proteins with conventional biochemical and molecular methods. From the genome sequence of the spirochete, *Borrelia burgdorferi*, more than 100 surface associated lipoproteins were identified. Based on genome size and the biology of its lifecycle, *Leptospira* are expected to have a significantly greater number of surface-associated targets. At present, less than 10 surface-associated proteins have been characterized through isolation of membrane extracts, purification and characterization of proteins in these extracts and molecular cloning of these protein targets (8-14) (12). Immunization with recombinant proteins for several identified targets, LipL32, OmpL1 and LipL41, induce partial, but not complete, protective responses (11, 12).

To develop a more comprehensive understanding of leptospiral protein expression we have used the humoral immune response during human leptospirosis as a reporter of protein antigens expressed during infection. The identification of leptospiral antigens expressed during infection has potentially important implications for the development of new serodiagnostic and immunoprotective strategies. Sera from patients with leptospirosis was used to identify clones from a genomic *Leptospira* DNA phage library which express immunoreactive polypeptides. A proportion of these clones were found to encode a novel family of membrane-associated *Leptospira* proteins. The identification of these polynucleotides and polypeptides and their application for diagnosis of leptospirosis and inducing an immune response to pathogenic spirochetes is the basis for this invention.

SUMMARY

The invention relates to DNA molecules in *Leptospira* and the polypeptides they encode which have repetitive bacterial Ig-like domains. The invention describes the isolation of three DNA molecules, originally derived from *L. kirschneri* and *L. interrogans*, which encode proteins, herein designated "BigL1", "BigL2" and "BigL3", that have molecular masses of approximately 110, 205 and 205 kDa, respectively, based on the predicted amino acid sequence of the polypeptides. The three proteins have 12-13 tandem repeat sequences of approximately 90 amino acids. Repeat sequences from BigL1, BigL2 and BigL3 are highly related (>90% amino acid sequence identity) to each other and belong to the family of bacteria Ig-like (Big) domains, moieties which are found in virulence factors of bacterial pathogens.

The DNA molecules that encode for *Leptospira* proteins with Big domains, herein called "bigL1", "bigL2" and "bigL3", can be inserted as heterologous DNA into an expression vector for producing peptides and polypeptides. Recombinant polypeptides can be purified from surrogate hosts transformed with such expression vectors. BigL1, BigL2 and BigL3-derived polypeptides are serological markers for active and past infection since sera from leptospirosis patients and animals infected or immunized with pathogenic *Leptospira* recognize isolated polypeptides.

Furthermore, BigL1, BigL2 and BigL3 polypeptides from recombinant or native antigen preparations are immunogenic. Antibodies obtained from experimental animals immunized with purified recombinant BigL1, BigL2 and BigL3 polypeptides recognize native antigen from *Leptospira*, and are useful for detecting pathogenic spirochetes in samples from subjects with a suspected infection.

In addition, BigL1, BigL2 and BigL3 polypeptides induce an immune response against pathogenic spirochetes. BigL1, BigL2 and BigL3-derived polypeptides; antibodies to these polypeptides; and polynucleotides that encode for BigL1, BigL2 and BigL3 may be used alone or combined with pharmaceutically acceptable carrier to treat or prevent infection with *Leptospira*. Since Big domains are present in proteins associated with virulence in other bacterial pathogens, these moieties may be used to treat or prevent infections unrelated to those caused by *Leptospira.*

In a first embodiment, the invention provides isolated DNA molecules for bigL1, bigL2 and bigL3 and the polypeptides that are encoded by these DNA molecules or have functionally equivalent sequences. In addition, a method is provided for producing an expression vector containing bigL1, bigL2 and bigL3 polynucleotides and obtaining substantially purified polypeptides derived from these sequences.

A second embodiment of the present invention is to provide pharmaceutical composition for inducing immune responses in subjects to pathogenic spirochetes, comprising an immunogenically effective amount of one or more selected antigens among the group consisting of BigL1, BigL2, BigL3 and polypeptides with functionally equivalent sequences in a pharmaceutically acceptable vehicle.

In a third embodiment, the invention provides a method for identifying a compound which binds to BigL1, BigL2, BigL3 polypeptides or polypeptides with functionally equivalent sequences that includes incubating components comprising the compound and BigL1, BigL2 or BigL3 polypeptide or polypeptides with functionally equivalent sequences under conditions sufficient to allow the components to interact and measuring the binding of the compound to the BigL1, BigL2 or BigL3 polypeptide or polypeptides with functionally equivalent sequences. Preferably, the inventive method is a serodiagnostic method utilizing sera from a subject with a suspected active or past infection with *Leptospira* or other related bacterial pathogen.

In a fourth embodiment, the invention provides a method for detecting pathogens in a sample which includes contacting a sample suspected of containing a pathogenic spirochete with a reagent that binds to the pathogen-specific cell component and detecting binding of the reagent to the component. In one aspect, the reagent that binds to the pathogen-specific cell component is an oligonucleotide for the identification of bigL1, bigL2 and bigL3 polynucleotide. In another aspect, the reagent that binds to the pathogen-specific cell component is an antibody against the BigL1, BigL2 or BigL3 polypeptide or polypeptides with functionally equivalent sequences.

In a fifth embodiment, the invention provides a kit useful for the detection of BigL1, BigL2, and BigL3 polypeptides or polypeptides with functionally equivalent sequences; bigL1, bigL2 and bigL3 polynucleotides; or antibodies that bind to BigL1, BigL2, BigL3, polypeptides or polypeptides with functionally equivalent sequences.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The foregoing and other objects, features, and advantages of the invention will become more apparent from the following detailed description, which proceeds with reference to the accompanying figures.

BRIEF DESCRIPTION OF THE DRAWINGS

FIG. 3 shows the polymerase chain reaction (PCR) amplification of DNA fragments from strains of five pathogenic species of *Leptospira*. Degenerate primers were designed based on the *L. kirschneri* and *L. interrogans* sequence encoding for the BigL3 region corresponding to positions 46-65 aa. PCR reactions were performed from purified DNA from five pathogenic (*L. kirschneri, borgpetersenii, interrogans, santarosai*, and *noguchi*) and two non-pathogenic species (*L. biflexi* and *wolbachii*).

Figure 1A:
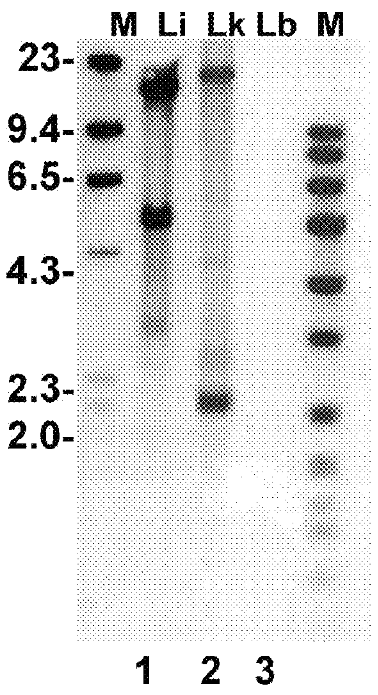
FIGS. 1A and 1B show a Southern blot analysis of bigL gene sequences in *Leptospira*. Genomic DNA (3 mcg/lane) from *L. interrogans* strain Fiocruz L1-130 (lanes 1), *L. kirschneri* strain Rm52 (lanes 2) and *L. biflexi* strain Patoc I (lanes 3) digested with NsiI and subject to agarose gel electrophoresis. After transfer to nitrocellulose membranes, blots were probed with DNA fragments that encode for BigL repetitive domains ($4^{th}$-$6^{th}$ repetitive domain of BigL3, FIG. 1A) and C-terminal regions of bigL1, bigL2 and bigL3, which are unique to each of these genes, respectively (FIG. 1B).

*leptospira* per lane; lanes 2, 4, 6 and 8) from cultured leptospires. Membranes were probed with pooled sera (dilutions 1:500 [lanes 4 and 5], 1:100 [lanes 6 and 7] and 1:2500 [lanes 8 and 9]) from rats immunized with rBigL3 from *E. coli* expressing a cloned DNA fragment of bigL3 from *L. interrogans*. Pre-immune sera was obtained prior to the first immunization and used in the immunoblot analysis as a control (lanes 2 and 3). The mobility (kDa) of molecular mass standards are shown on the left side of the figure.

Figure 10:
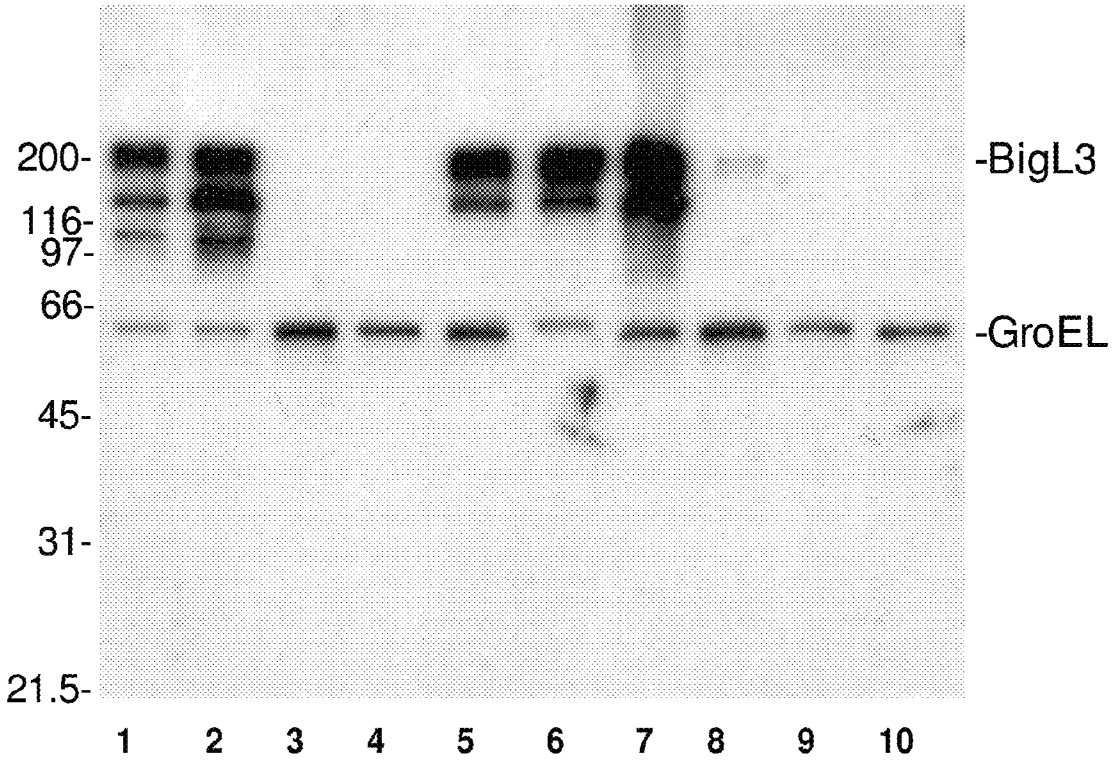

FIG. 10 shows the immunoblot reactivity of rabbit anti-rBigL3 antisera to native antigen from *Leptospira* strain lysates. Immunoblots were prepared with whole antigen preparations ($10^8$ *leptospira* per lane) of the following cultured strains: lane 1, *L interrogans* sv *pomona* (type kennewicki) strain RM211, low-passage; lane 2, *L. interrogans* sv canicola strain CDC Nic 1808, low passage; lane 3, *L. interrogans* sv *pomona* strain PO-01, high passage; lane 4, *L. interrogans* sv *bratislava* strain AS-05, high passage; lane 5, *L. kirschneri* sv *grippotyphosa* strain RM52, low passage; lane 6, *L. kirschneri* sv *grippotyphosa* strain P8827-2, low passage; lane 7, *L. kirschneri* sv *grippotyphosa* strain 86-89, low passage; lane 8, *L. kirschneri* sv *grippotyphosa* strain Moskva V, high passage; lane 9, *L. kirschneri* sv *mozdok* strain 5621, high passage; lane 10, *L. kirschneri* sv *grippotyphosa* strain RM52, high passage. Membranes were probed with sera from rabbits immunized with rBigL3 from *E. coli* expressing a cloned DNA fragment of bigL3 from *L. kirschneri* and, as a control measure, sera from rabbits immunized with recombinant *L. kirschneri* GroEL protein. The positions of native antigens corresponding to BigL3 and GroEL and the mobility (kDa) of molecular mass standards are shown on the left and right sides, respectively, of the figure.

DETAILED DESCRIPTION

For convenience, the meaning of certain terms and phrases employed in the specification, examples, and appended claims are provided below. Unless defined otherwise, all technical and scientific terms used herein have the same meaning as commonly understood by one of ordinary skill in the art to which this invention belongs.

BigL—are polypeptides of *Leptospira* sp. having tandem repeat sequences each of which are similar, according to their sequence homology, to bacterial immunoglobulin-like (Big) domains. Big domains are present in bacterial proteins, expressed in bacterial pathogens such as *E. coli, Yersinia* and *Bordetella*, which have virulence functions such as host cell adhesion.

Reference sequence—is a new sequence obtained by isolation from a natural organism or through genetic engineering and presents an accurate biological function, which is characteristic of the present invention.

Functionally equivalent sequences—are the sequences, related to a reference sequence, that are the result of variability, i.e. all modification, spontaneous or induced, in a sequence, being substitution and/or deletion and/or insertion of nucleotides or amino acids, and/or extension and/or shortening of the sequence in one of their ends, without resulting in modification of the characteristic function of the reference sequence. Functionally equivalent sequences encompass fragments and analogs thereof. In other words, sequences functionally equivalent are sequences that are "substantially the same" or "substantially identical" to the reference sequence, such as polypeptides or nucleic acids that have at least 80% homology in relation to the sequence of amino acids or reference nucleic acids. The homology usually is measured by a software system that performs sequence analyses (Sequence Analysis Software Package of the Genetics Computer Group, University of Wisconsin Biotechnology Center, 1710, University Avenue, Madison, Wis., 53705).

As we mentioned before, *Leptospira* antigens expressed during the host infection are important in the identification of targets for diagnosis tests and vaccines. The LipL32 protein is one of these targets and was identified as immunodominant antigen by the immune humoral response during the natural infection. However the sensitivity of serologic tests based upon detection of antibodies against LipL32 in patient sera during acute-phase illness with leptospirosis detection is limited (see Flannery, B: "Evaluation of recombinant *Leptospira* antigen-based Enzyme-linked Immunosorbent Assays for the serodiagnosis of Leptospirosis" *J. Clin. Microbiology* 2001; 39(9): 3303-3310; WO9942478).

The present invention is based on the identification of the family of proteins BigL associated with species of spirochetal bacteria, including those belonging to *Leptospira.*

According to the present invention, the BigL protein family was identified as targets of the host humoral immune response, generated during infection with pathogenic *Leptospira* or immunization with pathogenic *Leptospira* or recombinant BigL polypeptides. BigL polypeptides and polynucleotides that encode these polypeptides are useful as in diagnostic tests to identify naturally occurring infection in different species including humans and animal reservoirs. The diagnostic test based on those proteins presents improved sensitivity and specificity in relation to standard diagnostic tests or those that have been used in the published literature. The identification of leptospirosis in the initial phase. In addition BigL polypeptides can induce immune responses when used in a pharmaceutical composition for immunization.

In the present invention, the three BigL polypeptides are characterized with molecular weights 128.4 kD, 201.3 kD and 200.4 kD, based on the deduced amino acid sequence of the isolated polynucleotides, bigL1, bigL2 and bigL3, which encode for these polypeptides. The amino acid sequence of the BigL polypeptides has a signal sequence and a putative signal peptidase cleavage site largely conforming to the spirochetal lipobox; therefore BigL polypeptides are membrane-associated lipoproteins. The polypeptides of 128.4 kD, 201.3 kD and 200.4 kD are designated "BigL1", "BigL2" and "BigL3", respectively.

Although the BigL polypeptides of the present invention have been isolated originally of *Leptospira* sp, they are useful not just for induction of the immune response against the pathogenic organisms *Leptospira* sp., but also against other spirochetes bacteria and pathogens that have factors with Big domains. Additionally, BigL polypeptides can be used for the diagnosis of infections due to *Leptospira* sp., other pathogenic spirochetes and bacterial pathogens.

Several processes that incorporate state-of-the-art methodologies can be used to obtain polynucleotide sequences that encode for BigL polypeptides. These processes include, but they are not limited to, the isolation of DNA using hybridization of genomic libraries with probes to detect homologous sequences of nucleotides; screening of antibodies of expression libraries to detect fragments of cloned DNA with shared structural aspects; polymerase chain reaction (PCR) in genomic DNA using initiators able to recombine sequence of DNA of interest; and computer-based searches of sequence databases for similar sequences to that of the bigL polynucleotides.

In the present invention the identification of the antigens was based on knowledge that there is differential expression of *Leptospira* antigens during culture (in vitro) and during host infection (in vivo). Differential expression of *Leptospira* antigens is presumed to be important in host adaptation during infection. We used a strategy to identify immunoreactive antigens and therefore antigens expressed during host infection. Sera from patients infected with pathogenic *Leptospira* were used to select polynucleotide sequences from genomic *Leptospira* DNA library in lambda phage that encode for immunoreactive polypeptides.

The present invention identified and isolated three polynucleotides with nucleotide sequences corresponding to SEQ ID No: 1, SEQ ID No: 3 and SEQ ID No: 5, as well as the amino acid sequences of the respective polypeptides, BigL1, BigL2 and BigL3, encoded by such nucleotides.

Step 1—the Screening the Positive Clones Consisted Basically of the Following Steps:

(a) The DNA of a pathogenic *Leptospira* was cut with an appropriate enzyme and ligated into a specific site in the lambda phage genome. Host bacteria were infected with phage and the resulting clones, expressing recombinant polypeptides after induction with IPTG, were submitted to immunoblot protocol where a membrane of colony lysates was incubated with sera from patients with laboratory confirmed leptospirosis and then with a secondary antibody conjugated to horseradish peroxidase, which recognized human Ig. Positive clones were detected through an indicator reaction, for antigen-antibody complexes based on the production of color.

(b) The sequence of cloned and isolated polynucleotides was determined using phage vector-specific sequences as initiators of the sequencing reaction. Analysis of the clone sequences and the use of a primer walking strategy identified the complete nucleotide sequence for the genes that encode for BigL1, BigL2, and BigL3.

(c) Most of the obtained positive clones contain genes encoding proteins of thermal shock Hsp58 and DnaK and the protein of outer membrane LipL41. However, it was found clones containing genes encoding repetitions in tandem of 90 amino acids compared by Database of proteins family (Pfam) as proteins of bacterium, type immunoglobulin (Big). With the analysis of the clone sequences, were identified 3 genes containing 12 tandem repeats for bigL1 and 13 tandem repeats in bigL2 and bigL3.

Step 2—Subcloning Expression and Purification of the Protein

Drawing of two oligonucleotides with base in sequences of two proteins BigL

Amplification by PCR of the initial BigL portion encoding for part of the repetitive region, from those oligonucleotides Sequencing of the product of the amplification Subcloning of the region-encoding by the product sequenced Expression of the recombinant protein.

Purification of the recombinant protein.

Immunoblot analyses demonstrate that sera from leptospirosis patient and rodent reservoirs infected with pathogenic *Leptospira* produce antibodies primarily to the BigL domain repeats of the BigL polypeptides, indicating that they are the main antigenic regions recognized during infection.

In relation to the polypeptides of the present invention they consist of sequences of DNA, cDNA or RNA (and sequences of nucleic acids which are complementary), as well as their functionally equivalent sequence, i.e., those sequences that encode the whole or a part, of the polypeptides designated as BigL1, BigL2 and BigL3, but are non-identical due to variability.

The polypeptides and polynucleotides in the present invention consist of BigL1, BigL2 and BigL3 and the polynucleotides that encode these polypeptides; however they include, in addition, polypeptides and polynucleotides that have functionally equivalent sequence.

In the present invention, both polynucleotides and polypeptides may be of natural, synthetic or recombinant origin, having the necessary purity degree to grant to their biological activities.

The present invention also refers to the polynucleotides encoding for BigL1, BigL2 and BigL3 which are used in PCR reactions to obtain either complete or partial amplified DNA fragments of the bigL polynucleotides, for the purpose of detection of *Leptospira* in samples or expression of recombinant BigL polypeptides. In the case of initiators used for the polynucleotide amplification in the present invention, they are oligonucleotides made of two or more deoxyribonucleotides or ribonucleotides, natural or synthetic.

Each initiator is preferably constructed in order to be substantially similar to a flanking region of the sequence strand that is the target for amplification. In this sense, an initiator can be designated functionally equivalent if corresponding polymers can produce the same process, without being identical, facing the utilization or application considered.

Polynucleotide sequences of this invention can also be inserted in an expression vector, such as a plasmid, virus or other vehicle used for recombinant cloning, which is used by inserting or incorporating whole or partial nucleotide sequences that encode for BigL1, BigL2 and BigL3 or their functionally equivalent sequences. Such expression vectors contain a promoter sequence that facilitates the efficient transcription from genetic sequence in the host in which the vector is inserted. Such hosts can include prokaryotes or eukaryotes, including microorganisms such as yeast or insects and mammals. Such processes for the use of expression vectors construction and for the expression of recombinant sequences, properly so-called, are well known by experts in technique.

The present invention provides for a method to produce antibodies that bind to complete or partial polypeptides of BigL1, BigL2 and BigL3 or their functionally equivalent sequences. Such antibodies are useful as research and diagnostic tools in the study and diagnosis of spirochete infections in general, and more specifically in the development of diagnostics and therapeutics whether treatment or prevention, for leptospirosis. Such antibodies can be administered alone or as part of a pharmaceutical composition that uses these antibodies and a pharmaceutically acceptable carrier as part of anti-spirochetal therapeutic.

The invention relates to the use of pharmaceutical compositions of BigL polypeptides or the polynucleotides that encode for these polypeptides as vaccines, either as a vaccine for prevention of disease which induces an immunoprotective response to infection or colonization with pathogenic spirochetes or as therapeutic vaccine that provides a beneficial impact in reducing the duration or severity of the clinical course of illness in a subject due infected with a pathogenic spirochete or in reducing the reservoir state of a carrier of pathogenic spirochete such as in pigs, cows, rats or dogs that harbor and excrete pathogenic spirochetes for prolonged periods of time. Such compositions may be prepared with an immunogenically effective quantity of an antibody against BigL1, BigL2 and BigL3 respectively, or with one or more of BigL1, BigL2 and BigL3 isolated from the leptospiral pathogen or recombinant BigL polypeptides, or their functionally equivalent sequences, in excipients and additives or auxiliaries.

Another embodiment of present invention relates to the pharmaceutical composition used to induce an immune response to a pathogenic spirochete in an individual, particularly *Leptospira* sp., including an immunologically effective quantity of BigL1, BigL2 and BigL3 or of their functionally equivalent sequence in a pharmaceutically acceptable vehicle. As "individual" we refer to any mammal, including humans, rodents, domesticated and laboratory animals and livestock. As "quantity immunologically effective" we refer to quantity of BigL polypeptide antigen necessary to induce, in an individual, an immunological response against *Leptospira* or any other pathogenic spirochete or bacterial pathogen. The invention further provides a kit for:

1—detecting one of polypeptides, BigL1, BigL2 and BigL3, or their functionally equivalent sequences;

2—detecting nucleic acid encoding for BigL1, BigL2 and BigL3 or their functionally equivalent sequences;

3—detecting antibodies for such polypeptides, BigL1, BigL2 and BigL3, or their functionally equivalent sequences.

The kit used for detection of BigL polypeptides includes those that use a vehicle containing one or more receptacles with a first receptacle containing a linking reagent to BigL1, BigL2 and BigL3 or to their functionally equivalent sequences.

The kit used for detection of polynucleotides that encode BigL polypeptides includes those that use a vehicle containing one or more receptacles with a first receptacle containing a polynucleotide that hybridizes to the nucleic acid sequence that encodes BigL1, BigL2 and BigL3 or to their functionally equivalent sequences.

The kit useful for detecting antibodies against BigL polypeptides includes those that use a vehicle containing one or more receptacles with a first receptacle containing a polypeptide of BigL1, BigL2 and BigL3 or of their functionally equivalent sequences.

The present invention will be now described with reference to the Examples, which should not be considered as limiting of the present invention.

EXAMPLE 1

Example 1A

Bacterial Strains, Plasmids and Media

*Leptospira kirschneri* serovar *grippotyphosa*, strain RM52, was isolated during an outbreak of porcine abortion in 1983. *L. interrogans* serovar *copenhageni*, strain Fiocruz (L1-130), was isolated from the bloodstream of a human leptospirosis patient. *L. kirschneri* serovar *grippotyphosa* strain RM52 and other leptospiral strains were obtained from the National Leptospirosis Reference Center (National Animal Disease Center, Agricultural Research Service, U.S. Department of Agriculture, Ames, Iowa). Leptospiral strains were cultivated at 30° C. in Johnson-Harris bovine serum albumin-Tween80 medium (Bovuminar PLM-5 Microbiological Media, Intergen (2)). Low-passage samples of the RM52 isolate were either stored in liquid nitrogen or passaged in liquid medium at least 200 times to generate a high-passage form. The high-passage strain was unable to produce a lethal infection in hamsters at any dose and was only able to infect hamsters at a dose of $10^7$ by intraperitoneal inoculation.

*Escherichia coli* XL1-Blue MRF'ΔmcrA)183ΔmcrCB-hsdSMR-mrr)173 endA1 supE44 thi-1 recA1 gyrA96 relA1 lac [F'proAB lacI$^q$ZΔM15 Tn10 (Tetr)] (Stratagene) and *E. coli* PLK-F' (endA1 gyrA96 hsdR17 lac recA1 relA1 supE44 thi-1 [F' lacI$^q$ZΔM15]) were used as the host strains for infection with the λZap II (Stratagene) and λTriplEx (Clontech) vectors, respectively. *E. coli* SOLR (e14$^-$[mcrA], Δ[mcrCB-hsdSMR-mrr]171 sbcC recB recJ umuC::Tn5[Kan$^r$] uvrC lac gyrA96 relA1 thi-1 endA1 λ$^r$, [F' proAB lacI$^q$ZΔM15], Su$^-$ [non-suppressing]] and *E. coli* BM25.8 (supE44 thi Δlac-proAB [F' traD36 proAB$^+$ lacI$^q$ZΔM15] λimm434(kan$^r$) P1(cam$^r$) hsdR($r^{K12-}m^{K12-}$)) were used for in vivo excision of the pBluescript and pTriplEx phagemids, respectively. BLR(DE3)pLysS [F$^-$ ompT hsdS$_B$ ($r_B$-$m_B$–) gal dcm_(srl-recA)306::Tn10(TcR) (DE3) pLysS(CmR)] (Novagen) was used as the host strain for the pRSET expression vector (Invitrogen). *E. coli* strains were grown in LB supplemented with 100 μg/ml ampicillin, 100 μg/ml carbenicillin, or 25 μg/ml chloramphenicol where appropriate. Antibiotics were purchased from Sigma.

Example 1B

Isolation and Characterization of bigL Genes

This example illustrates the identification and isolation of the bigL genes. Genomic DNA was prepared from virulent, low-passage *L. kirschneri*, serovar *grippotyphosa*, strain RM52 by the method of Yelton and Charon (15). Genomic DNA was prepared from a clinical isolate of *L. interrogans*, serovar *copenhageni*, strain Fiocruz L1-130, using a kit to genomic DNA (Qiagen). The QIAquick® PCR Purification Kit (Qiagen) was used to obtain purified DNA. The genomic DNA was partially digested with Tsp509I and ligated to λTriplEx arms following the instructions provided (Clontech). The Gigapack® III Gold Packaging Extract (Stratagene) was used to package ligated, digested genomic DNA into lambda heads. The phage titer of the library was determined by infection *E. coli* XL1-Blue.

For screening of the genomic library, approximately $10^3$ pfu were plated on a lawn of *E. coli* XL1-Blue, transferred to nitrocellulose membrane (Schleicher & Schuell), sensibilized with IPTG and processed as recommended (Schleicher & Schuell). The nitrocellulose filter was blocked with 5% skimmed milk in Tris-buffered saline (pH 7.8) with 0.05% Tween 20 (TBST) or phosphate-buffered saline (pH 7.4) with 0.05% Tween 20 (PBST), and incubated for 1 hour with pooled sera, diluted 1:50, from patients with laboratory-confirmed leptospirosis. Sera were collected from patients, identified in urban epidemics in Brazil between 1996 and 1999, during the convalescent-phase of illness, and were pre-absorbed with *E. coli* lysates prior to use to remove antibodies to *E. coli*. Membranes were washed three times with TBST or PBST, and incubated for more than 1 hour with rabbit or goat anti-human immunoglobulin antibody conjugated with alkaline phosphatase (Sigma) in the dilution of 1:1000. Detection with NBT (0.3 mg/ml) and BCIP (0.15 mg/ml) or development with the ECL Western Blot Detection Reagents (Amersham) followed by exposure to Hyperfilm (Amersham) was used to identify plaques with antigen-antibody complexes.

Each positive plaque was stored at 4° C. in 1 ml SM (0.1 M NaCl, 8 mM $MgSO_4$, 50 mM Tris-HCl pH 7.5; 0.01% in gelatin, with 1-2 drops of chloroform. The lambda plaque clones that reacted with pooled sera were subjected to two additional stages of purification. The genomic DNA fragments inserted into lambda bacteriophage were excised by infecting *E. coli* SOLR or BM25.8 strains with the lambda clones as described by the supplier (Stratagene and Clontech, respectively).

The sequence of the first 500-700 nucleotides of the insert was obtained using a vector-specific primer that links adjacent to the insert. Nucleotide sequence analysis of 131 clones identified 13 that had DNA fragment inserts, found to encode tandem repeats approximately 90 amino acids in length. Each of the repeat sequences were subsequently identified in Pfam 6.6 (available online at pfam.wustl.edu/) to belong to the Big2 family Big2 family of bacterial immunoglobulin-like (Big) domains.

To identify sequences that encode full-length proteins according to the predicted amino acid sequence, the nucleotide sequences of the clones were assembled from individual sequences obtained by a combination of primer walking and sequencing of nested deletions. The deletions were generated from the plasmid clones by removal of restriction fragments extending from inside the insert into the multicloning sites flanking the insert. Oligonucleotides were synthesized and obtained from GIBCO BRL or Operon. Inverse PCR (iPCR) was performed to obtain sequences containing the remainder of the genes and flanking DNA. The UCLA Core Sequencing Facility, the Yale/Keck Core DNA Sequencing Facility and the University of California at Berkeley Sequencing Facility performed the sequencing reactions.

Figure 2:
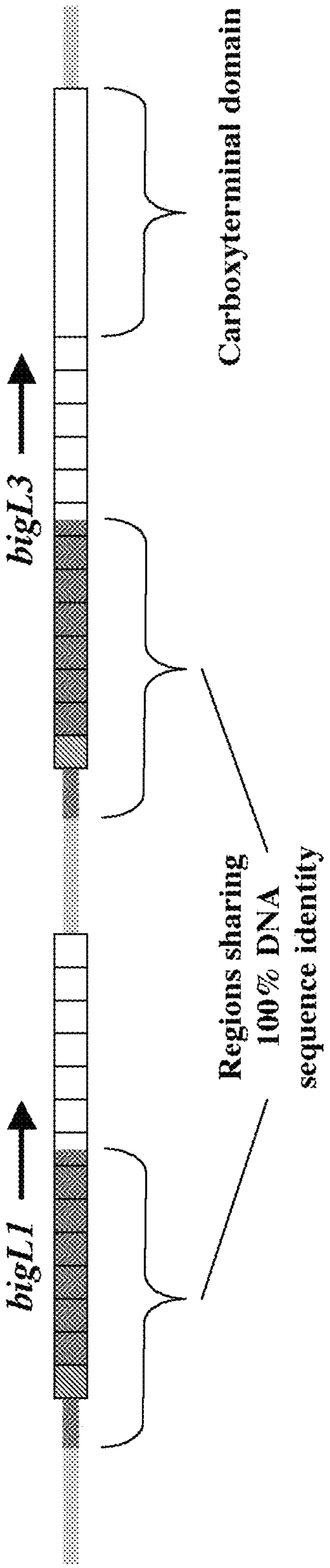
FIG. 2 shows a schematic diagram of the genomic organization of the region encoding the BigL1 and BigL3 proteins in *L. kirschneri*. The BigL1 protein would contain a signal peptide (hatched box) and thirteen 90-amino-acid bacterial immunoglobulin-like domains (solid boxes). The BigL3 protein would contain a signal peptide, twelve 90-amino-acid bacterial immunoglobulin-like domains, and a 793 amino acid carboxy-terminal (C-terminal) domain. The locations of the 2156 bp region of 100% DNA sequence identity are shown. The organization of the region depicted was conserved in *L. interrogans* and *L. kirschneri.*

Two *L. kirschneri* clones and four *L. interrogans* clones were found to encode a gene which we designate bacterial immunoglobulin-like Leptospiral protein one, bigL1. The complete nucleotide sequence of *L. kirschneri* bigL1 and the predicted amino acid sequence of the gene product is shown in SEQ ID NO: 1 and SEQ ID NO: 2. Six *L. kirschneri* clones were found to encode a second gene which we designated bigL2. The complete nucleotide sequence of *L. kirschneri* bigL2 is shown in SEQ ID NO: 3. *L. kirschneri* bigL2 appears to be a pseudogene, an extra adenine residue occurs at nucleotide 1011 resulting in a frameshift mutation and downstream TAG stop codon. However, the antibody screening with pooled patient sera was able to identify lambda clones with DNA fragments encoding bigL2 gene products, presumably since the cloned fragments did not have the frameshift mutation and were inserted in an orientation that allowed expression of a product that was recognized by patient sera. The predicted amino acid sequence of the *L. kirschneri* bigL2 gene product, without the frameshift mutation, is shown in SEQ ID NO: 4. A fifth *L. interrogans* clone was found to encode several Big repeats initially thought to belong to BigL1. However the upstream DNA encoded by this fifth *L. interrogans* clone was found to differ from the sequence upstream of bigL1. Sequencing the regions flanking the bigL1 gene revealed that the fifth *L. interrogans* clone corresponded to a third gene, designated bigL3, downstream of bigL1 (FIG. 2). The complete nucleotide sequence for bigL3 was obtained from *L. kirschneri* DNA and is shown in SEQ ID NO: 5. The predicted amino acid sequence of the *L. kirschneri* bigL3 gene product is shown in SEQ ID NO: 6.

All three bigL genes encode a signal peptide and putative signal peptidase cleavage site largely conforming to the spirochetal lipobox, as previously defined (Haake, D. A. 2000. Spirochetal lipoproteins and pathogenesis. Microbiology. 146:1491-1504). Comparison of the sequences of known spirochetal lipoproteins indicates that the spirochetal lipobox is much more loosely defined than the *E. coli* lipobox. For example, while most *E. coli* lipoproteins have Leu in the −3 position relative to Cys, spirochetal lipoproteins may also have a number of other hydrophobic amino acids in this position, including Val, Phe, and Ile. *E. coli* experiments involving site-specific mutagenesis of amino acids following cysteine indicate that acidic residues cause sorting of lipoproteins to the cytoplasmic membrane. Sequence analysis of leptospiral lipoproteins indicates that a similar sorting signal is present in these bacteria. For example, LipL31 is the only lipoprotein having an unopposed negative charge in the first two amino acids following cysteine, and is also the only lipoprotein sorted exclusively to the cytoplasmic membrane. Like the outer membrane lipoproteins LipL32 and LipL41, the BigL proteins have uncharged amino acids in the +2 and +3 positions, indicating that they would be sorted to the outer membrane.

Following their signal peptides, all three proteins would contain a series of tandem repeats, approximately 90-amino-acids in length. The mature BigL1 protein would consist almost entirely of thirteen repeats, while in contrast BigL2 and BigL3 contain twelve repeats followed by large carboxy-terminal domains. Though there is a high degree of sequence variation among the 31 unique repeats found in the three proteins, all of the repeats were identified by the Pfam database as bacterial immunoglobulin-like Big protein family with E-values as low as $4\times e^{-30}$.

The *L. interrogans* and *L. kirschneri* versions of bigL1, bigL2, and bigL3 were highly related, with >90% DNA and amino acid sequence identity. In both species there is a region of DNA sequence identity involving the 5' ends of bigL1 and bigL3 (FIG. 2). The region of sequence identity begins extends from the initial ATG start codon to position 1890 bp in both genes. The large region of DNA sequence identity between bigL1 and bigL3 results in an identical amino acid sequence for the first 630 amino acids (positions 1-630) of BigL1 (SEQ ID NO: 2) and BigL3 (SEQ ID NO: 6). This region of identity corresponds to the first six BigL domain repeats.

EXAMPLE 2

Example 2A

Characterization of the bigL Genes and Detection of bigL DNA and RNA

This example illustrates the distribution of multiple copies of bigL genes among *Leptospira* species and methods to detect bigL DNA and RNA in samples.

Southern Blot Analysis

Southern blot analysis was performed to identify multiple copies of bigL genes in genomic DNA from *L. interrogans* strain Fiocruz L1-130, *L. kirschneri* strain RM52, and *L. biflexi* strain Patoc I. DNA restriction and modifying enzymes were purchased from New England Biolabs. Genomic DNA was extracted from 500 ml of 7-day cultures of *Leptospira* cells with the Blood and Cell Culture kit (Qiagen, Valencia, Calif.). Approximately 3 mcg of DNA was digested with 5-20 units of NsiI overnight in a final volume of 50 mcl. DNA was then purified with phenol:chloroform:isoamyl and precipitated with 100% cold ethanol and 3M sodium acetate pH and washed with 70% ethanol. Purified DNA was then re-digested with 5-20 units PacI overnight in a final volume of 25 mcl. The double digested DNA was separated in a 0.8% agarose gel at 20V overnight. The gel was then incubated twice for 30 minutes in denaturing buffer (1.5 M NaCl, 0.5 N NaOH), and twice for 30 minutes in neutralization buffer (1M Tris (pH 7.4) 1.5 M NaCl). Genomic DNA was transferred onto a positively charged nylon membrane (Roche Molecular Biochemicals, Indianapolis, Ind.) according to the method described by Southern.

Probes were synthesized with the PCR Dig Probe Synthesis kit (Roche, Manheim, Germany). Reactions were assembled according to the manufacturer in a final volume of 50 mcl. Temperature cycles for the amplification were 94° C. for 5 min, 94° C. for 30 sec, 57° C. for 30 s min, and 72° C. for 1 min, with a final extension time of 7 min after a total of 35 cycles. Probe sequences were as follows: to amplify the bigL DNA fragments that code for BigL repetitive domains, a bigL3 DNA sequence was selected that corresponds to the region that encodes for BigL3 repetitive domains 4-6, BigL3_395 gat-ttt-aaa-gtt-aca-caa-gc (SEQ ID NO: 11) and BigL3_573 aaa-ccg-gac-tac-tta-cct-ttc-c (SEQ ID NO: 12); and to amplify bigL DNA fragments that are specific for each of the bigL genes, sequences that encode for C-terminal regions of the BigL gene products were selected: BigL1.2078p, tta-cgg-cta-cag-gta-ttt-tta-cg (SEQ ID NO: 13) and BigL1.2691p att-gga-aga-ttt-cca-agt-aac-c (SEQ ID NO: 14), BigL2.5121p tat-cta-cgc-tgc-aaa-tgg (SEQ ID NO: 15) and BigL2.5865p ttg-ttg-gcg-ata-cgt-ccg (SEQ ID NO: 16), BigL3.5071p cat-aac-tct-cct-cat-aac-a (SEQ ID NO: 17) and BigL3.5548p tat-gta-gag-ata-aga-tcc (SEQ ID NO: 18).

The UV Crosslinked membrane was subject to prehybridization at 42° C. for 1 hour in Dig Easy Hybridization solution (Roche). Prior to hybridization, the Dig labeled probes were boiled for 10 minutes and rapidly transferred to ice for 5 minutes. The denatured probes were mixed with hybridization solution and incubated overnight with the membrane at 42° C. Following hybridization, the membranes were washed twice for 5 minutes at room temperature with 2×SSC (NaCl, Sodium Citrate), 0.1% SDS. The membranes were then washed twice for 30 minutes at 42° C. with 0.1 SSC, 0.1% SDS. Membranes were exposed for 1-3 minutes to Biomax ML film (Eastman Kodak, Rochester, N.Y.) for the detection of chemiluminescent products.

Figure 1B:
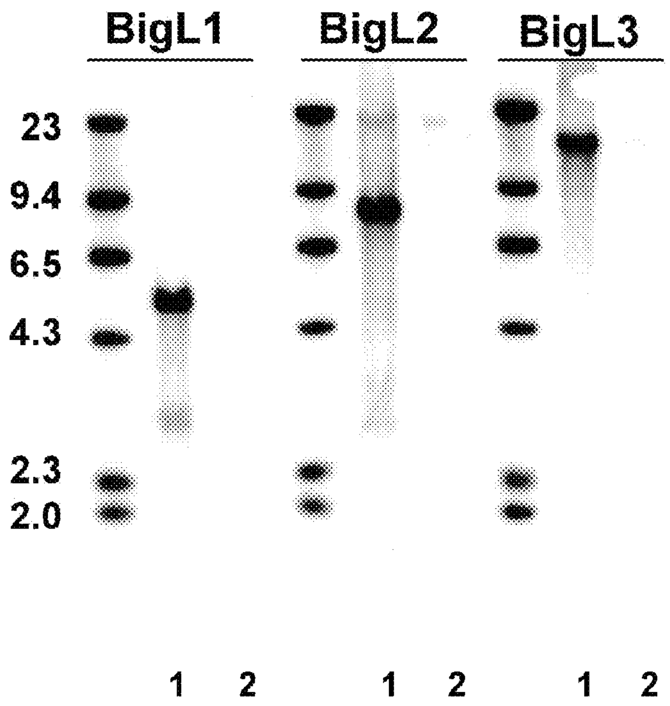

FIGS. 1A and B show the results of the Southern blots. Probes corresponding to DNA sequences that encode BigL repeats hybridized to multiple DNA fragments in *L. kirschneri* and *interrogans* (FIG. 1A). In contrast, hybridization was not identified with digested genomic DNA from the non-pathogenic *L. biflexi*. Probes based on sequences that encode for specific C-terminal regions for each of the *L. interrogans* bigL gene products hybridized to one unique fragment in digested *L. interrogans* genomic DNA, therefore confirming that there are one copy of each of the three bigL gene identified in Example 1 (FIGS. 1B). These results illustrate a method of identifying specifically pathogenic *Leptospira* based on detection of DNA fragments not found in non-pathogenic *Leptospira*.

Example 2B

PCR Detection of bigL Gene Sequences in *Leptospira* Genomic DNA

This example illustrates the distribution of bigL gene in pathogenic *Leptospira*. In order to detect bigL genes in other *Leptospira* species, degenerate primers were designed based on an alignment for bigL genes from *L. kirschneri* strain RM52 and *L. interrogans* strain Fiocruz L1-130, identified in Example 1. The sequence of the "upstream" primer, designated BigL-1up, is 5'-(GC)AAAGTTG(TC)(AG)(TC)G(TG)CTTGGCC-3' corresponding to positions 46-65 in bigL1 and bigL3 (SEQ ID NO: 1 and 5), relative to A of start codon. The sequence of the "downstream" primer, designated BigL-2dn, is 5'-(GC)(AT)ACC(AG)TC(CT)GAAAA(AG)AT(AT)CC-3' corresponding to positions 506-487 in bigL1 and bigL3 (SEQ ID NO: 1 and 5), relative to A of the start codon. Each primer is 20 nucleotides long. These primers were designed to anneal to bigL2 at positions 97-116 and 590-571 relative to the A in bigL2's start codon (SEQ ID NO: 3).

PCR reactions were performed with purified genomic DNA from high and low-passage strains of *Leptospira*. In FIG. 3, amplified DNA fragments were identified in PCR reactions with genomic DNA of strains in all four pathogenic species evaluated. Fragments had the predicted electrophoretic mobility based on the sequences of bigL1/bigL3 (461 bp) and bigL2 (494 bp). Amplified DNA fragments were not identified in the two non-pathogenic *Leptospira* species evaluated. Therefore this example illustrates the application of this PCR method for identifying specifically DNA from pathogenic *Leptospira* in samples.

Example 2C

Reverse Transcriptase-Polymerase Chain Reaction (RT-PCR) Detection of *Leptospira* bigL RNA This example illustrates the detection of bigL RNA in samples. *L. kirschneri* strain RM52 was grown to late exponential phase, and total RNA was extracted from $1\times10^{10}$ leptospiral cells using the hot-phenol method and resuspended in water following ethanol precipitation. ~2 μg of leptospiral RNA was digested with 6 units of DNase I (Ambion) in 70 μl DNase I buffer (10 mM Tris-HCl pH 7.5, 25 mM $MgCl_2$, 1 mM $CaCl_2$ in 1× RNA secure from Ambion) for 30 min at 37°. To inactivate DNase I, 1.75 μl of 25 mM EDTA was added to terminate the reaction, and the enzyme was heat killed for 5 min at 70°. RT-PCR was performed using ~200 ng leptospiral RNA and Omniscript RT as described (Qiagen). The following primers were used to prime the reverse transcriptase reaction:

```
bigL1,
                                    (SEQ ID NO: 19)
5'-CGCAGAAATTTTAGAGGAACCTACAG-3'

bigL2,
                                    (SEQ ID NO: 20)
5'-TTTGACTCCAAGACGCAGAGGATGAT-3'

bigL3,
                                    (SEQ ID NO: 21)
5'-ATTTTCAAGATTTGTTCTCCAGATTT-3';

lipL45,
                                    (SEQ ID NO: 22)
5'-ATTACTTCTTGAACATCTGCTTGAT-3'
```

The RT reactions were subjected to DNA PCR using Taq polymerase (Qiagen). Prior to PCR, the following primers were added to the reactions:

```
bigL1,
                                    (SEQ ID NO: 23)
5'-CTGCTACGCTTGTTGACATAGAAGTA-3'

bigL2,
                                    (SEQ ID NO: 24)
5'-TAGAACCAACACGAAATGGCACAACA-3'

bigL3,
                                    (SEQ ID NO: 25)
5'-ATCCGAAGTGGCATAACTCTCCTCAT-3'

lipL45,
                                    (SEQ ID NO: 26)
5'-TGAAAAGAACATTACCAGCGTTGTA-3'
```

Along with the primers added for reverse transcription, PCR products of 500 bp, 479 bp, 440 bp, and 438 bp are expected. To perform PCR, the reaction mixtures were placed in a Techne Progene thermocycler. An initial denaturation step of 95° for 1 min was followed by 30 cycles of denaturation at 95° for 30 sec, annealing at 53° for 30 sec, and extension at 72° for 30 sec. A final 72° incubation for 30 sec was then performed.

Figure 4:
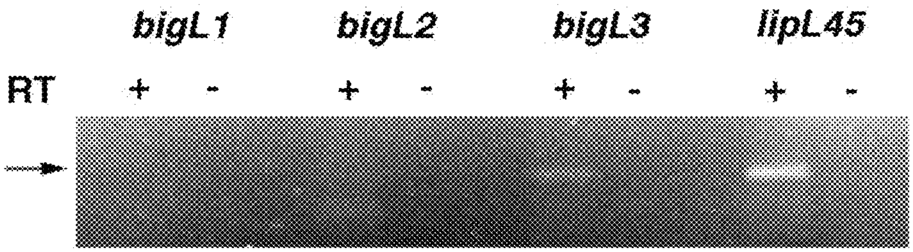
FIG. 4 shows amplified products from RT-PCR of RNA extracts of *L. kirschneri* with bigL1, bigL2 and bigL3 specific primers. Reverse transcription reactions (lanes "+") were performed on RNA extracts of cultured leptospires and then subject to a polymerase chain reaction (PCR) amplification step with primers that bind to unique sequences within bigL1, bigL2 and bigL3. Amplification with primers based on sequences within lipL45 was performed as a control reaction as were PCR reactions for which samples were not subjected to the reverse transcription step.
Figure 5:
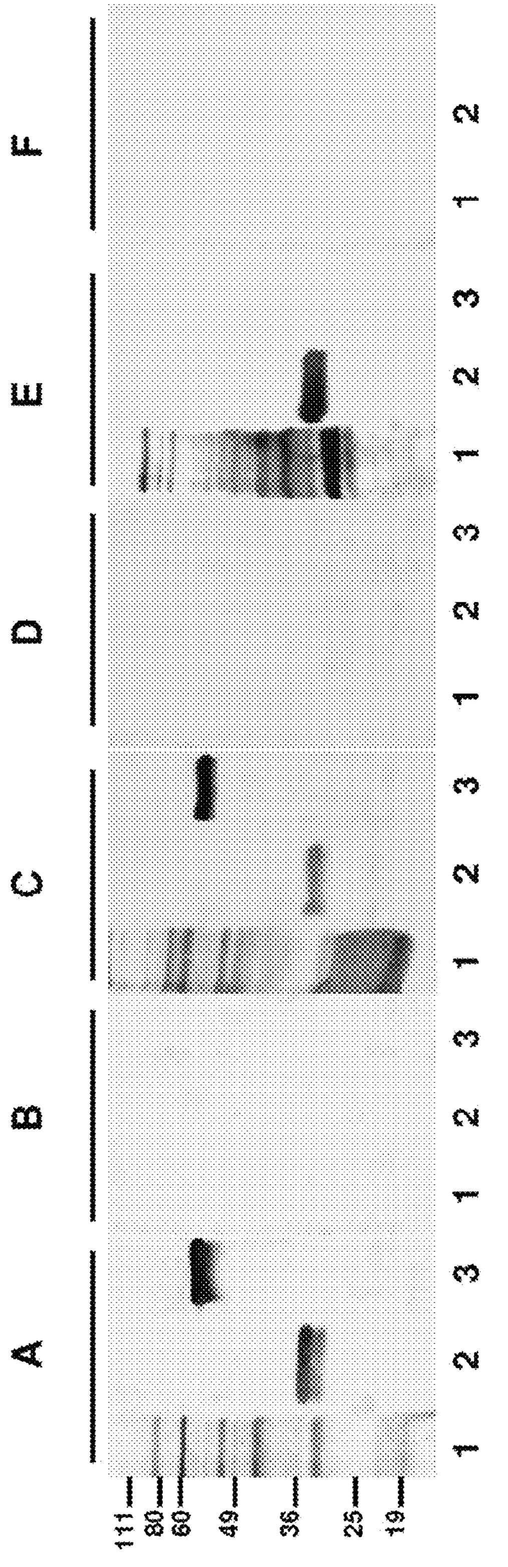
FIG. 5 shows the immunoblot reactivity of pooled sera from patients and animal reservoirs infected with pathogenic *Leptospira* and laboratory animals immunized with whole *L. interrogans* antigen preparation to recombinant BigL3 protein (rBigL3). Western blot analysis was performed with purified rBigL3 (1 mcg per lane, lanes 3). Membranes were probed with sera from patients with leptospirosis (lane A), healthy individuals (lane B), captured rats that are colonized with *L. interrogans* (lane C), captured rats that are not colonized with *L. interrogans* (lane D), laboratory rats immunized with whole antigen preparations of in vitro cultured *L. interrogans* (lane E) and pre-immune sera from the laboratory rats collected prior to immunization (lane F). Reactivity to whole *L. interrogans* antigen preparation (lanes 1) and recombinant LipL32 protein (rLipL32, lanes 2) is shown for comparison. The numbers on the left indicate the positions and relative mobilities (kDa) for molecular mass standards (Invitrogen).
Figure 6A:
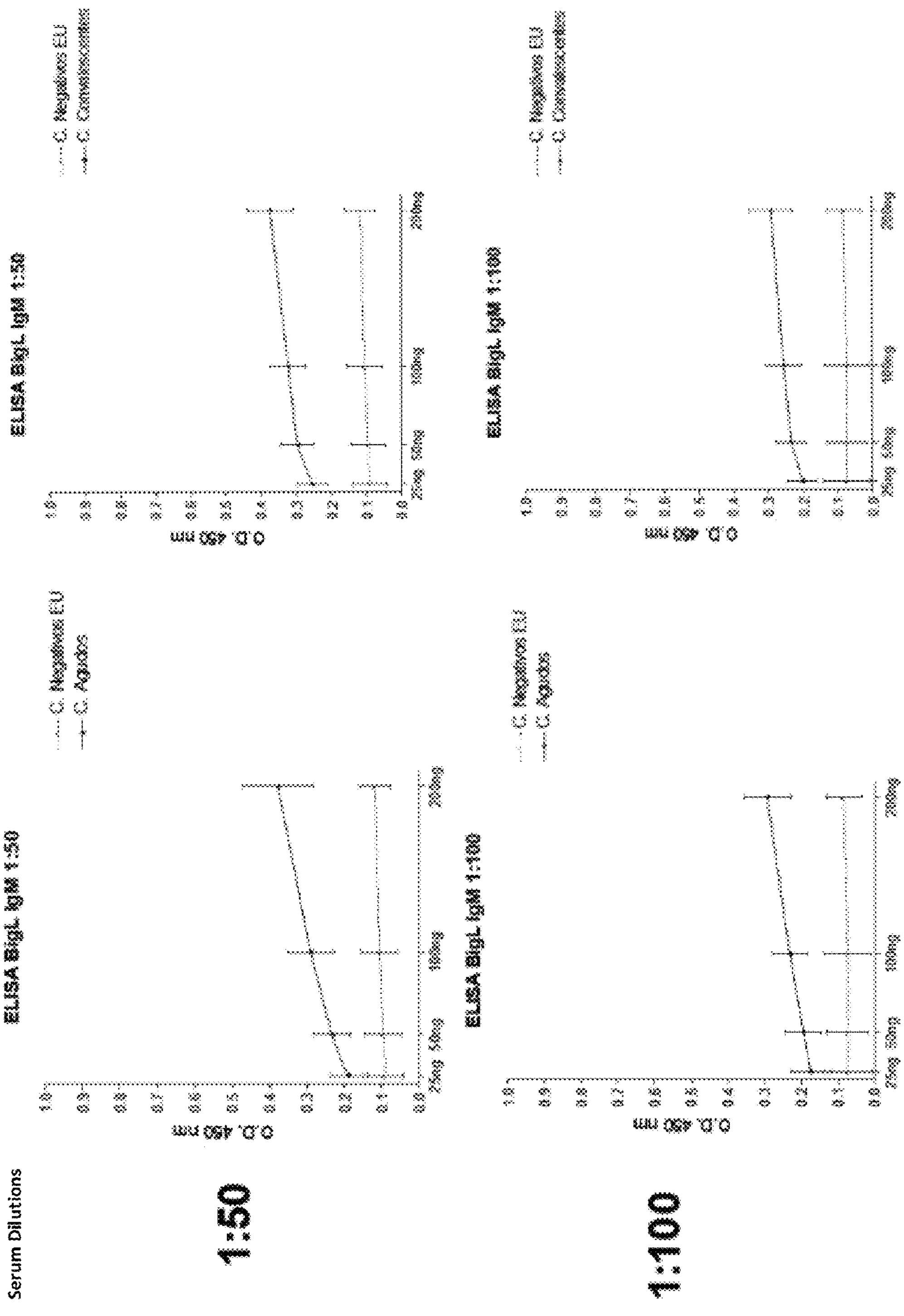
FIGS. 6A-6D shows an ELISA evaluation of individual patient seroreactivity to rBigL3 during the acute (left hand graph in each pair) and convalescent (right hand graph in each pair) phase of illness with leptospirosis. Sera from 4 leptospirosis patients (unbroken lines) and 4 healthy individuals (broken lines), at dilutions of 1:50, 1:100 and 1:200, were incubated with RBigL3 (25-200 ng/well). Mu and gamma chain specific antibodies conjugated to horseradish peroxidase were used to determine IgM and IgG seroreactivity, respectively. Mean absorbance values (OD 450 nm) and standard deviations are represented in the graphs.
Figure 6B:
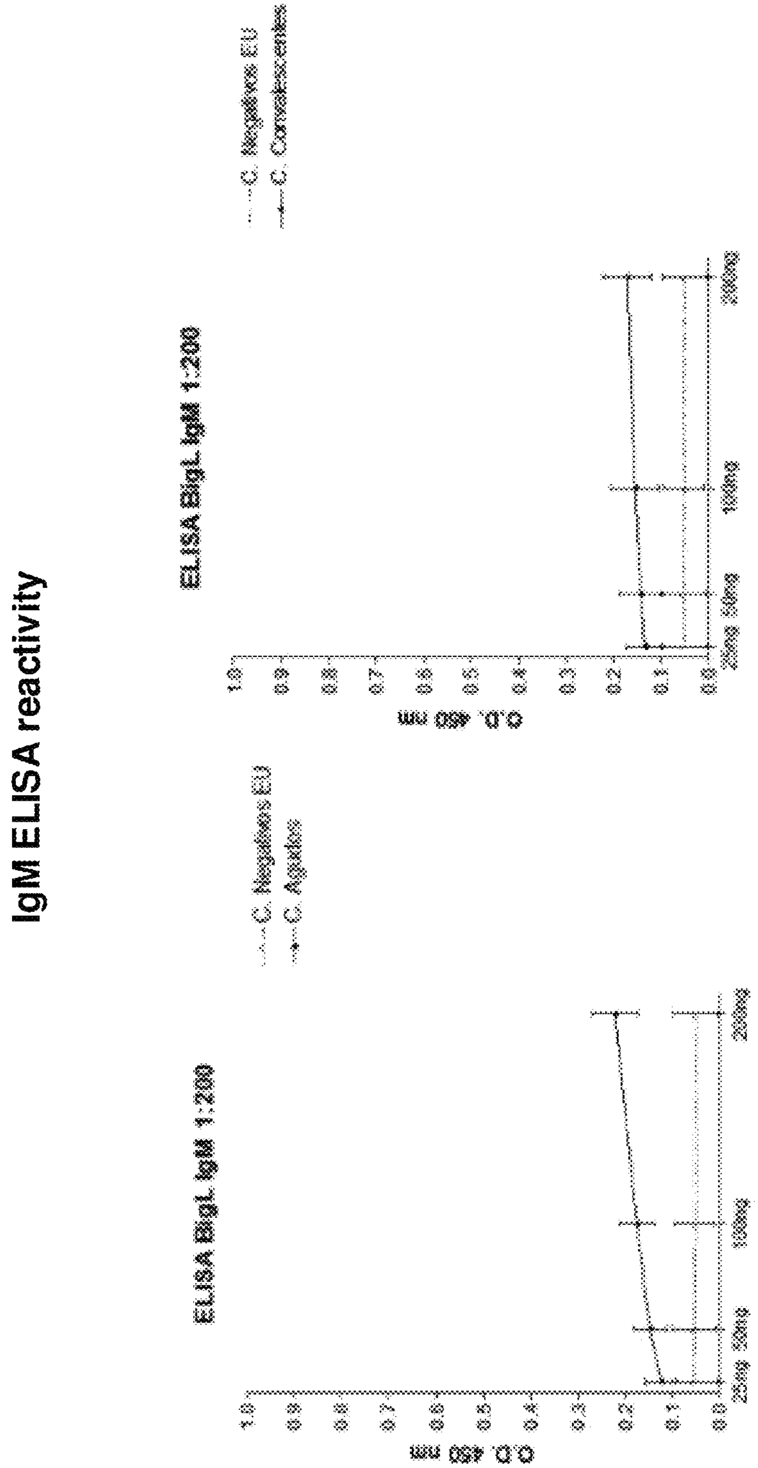
Figure 6C:
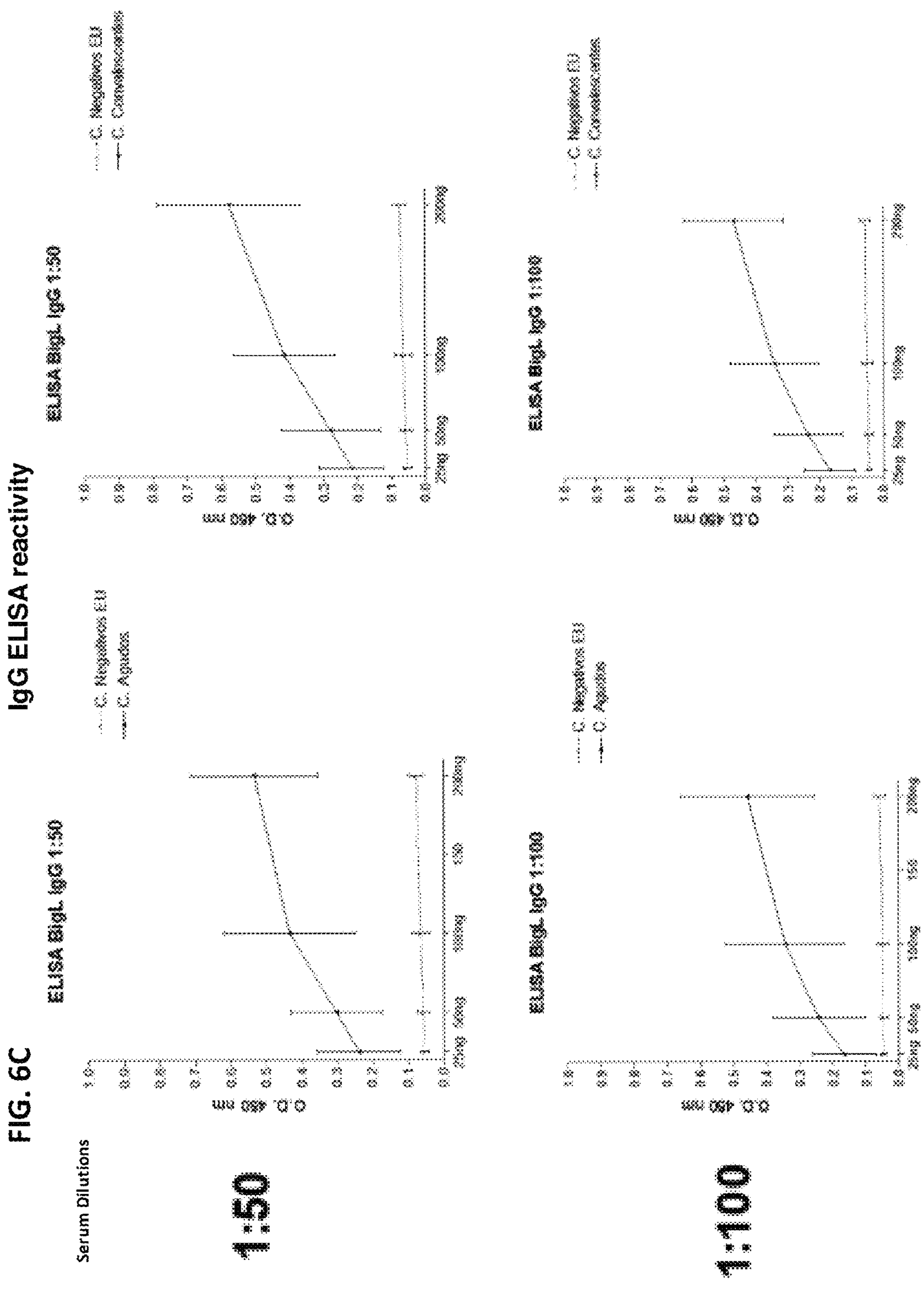
Figure 6D:
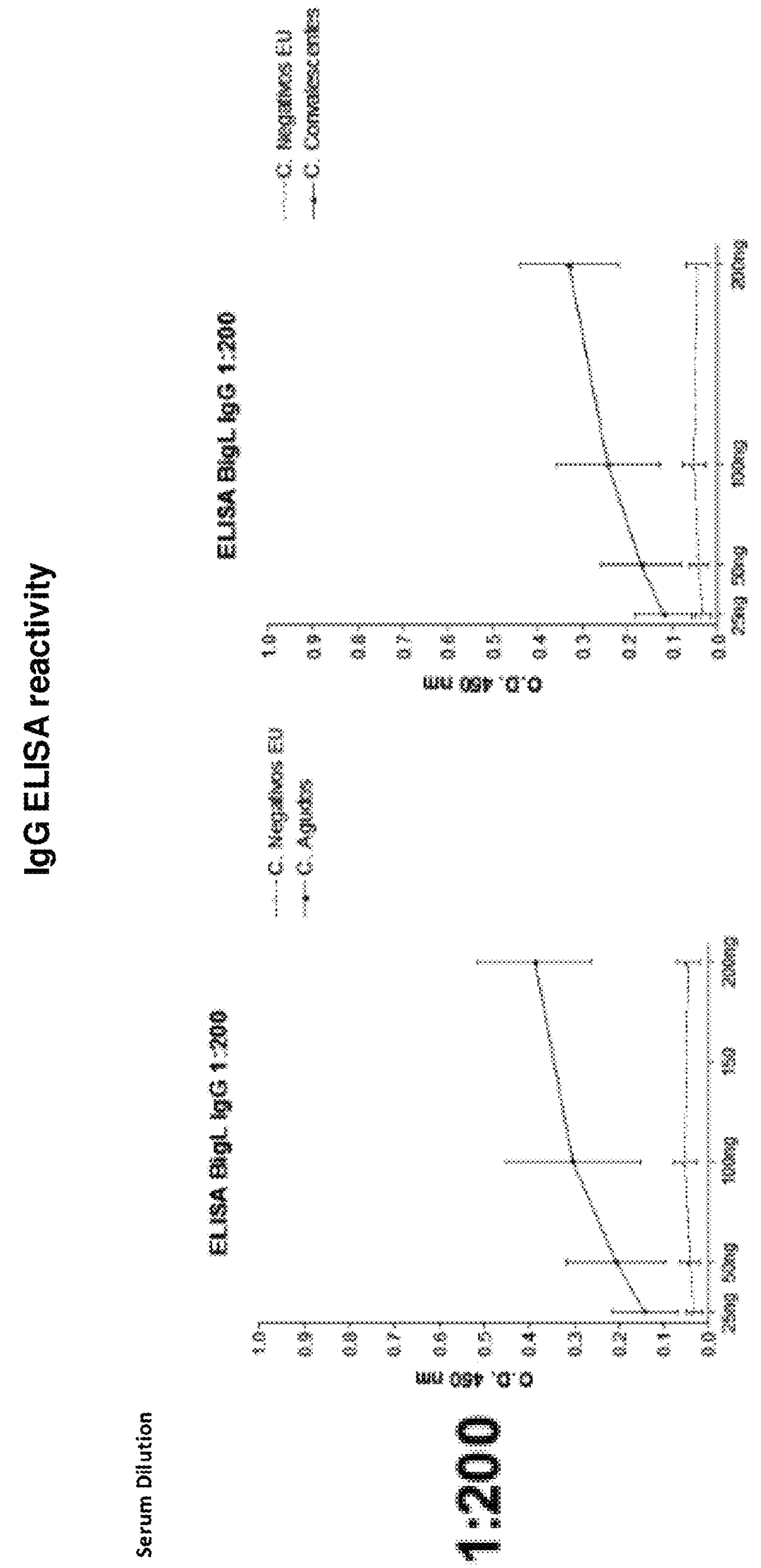

The results in FIG. 4 show that RT-PCR method can detect BigL3 transcripts and the control LipL46 transcripts. BigL1 and BigL2 transcripts were not identified indicating that whereas BigL3 is expressed in *Leptospira*, BigL1 and BigL2 may not be. Furthermore, these results demonstrate the application of the RT-PCR method to identify specific BigL gene transcripts in samples.

EXAMPLE 3

Expression and Purification of Recombinant BigL Proteins

This example illustrates the use of the DNA sequences of bigL genes to express and purify recombinant BigL polypeptides. Two pairs of oligonucleotides were designed for use in expressing two regions of *L. interrogans* BigL3. The first region was a region within BigL3 corresponding to the 2nd to 6th repetitive domains and corresponded to positions 131-649 of SEQ ID NO: 6 in the *L. kirschneri* BigL3DNA sequence. Oligonucleotides were designed based upon sequence of lambda *L. interrogans* BigL3 clones identified in Example 1 and their sequence are:

```
45B-1
                                    (SEQ ID NO: 27)
5'-ATGGGACTCGAGATTACCGTTACACCAGCCATT-3'

45B-2
                                    (SEQ ID NO: 28)
5'-ATTCCATGGTTATCCTGGAGTGAGTGTATTTGT-3'
```

PCR amplification with oligonucleotides 45B-1 and 45B-2 and purified *L. interrogans* genomic DNA was performed to obtain DNA fragments. These fragments were digested with XhoI and NcoI Enzymes (New Biolabs) and then ligated into the pRSETA expression vector (Invitrogen) (16). The cloned product was sequenced using vector specific primers and primer walking and the sequence of the 1557 bp product is shown in SEQ ID NO: 7. The predicted sequence of the encoded 519 amino acid polypeptide, designated BigL3 region 1, is shown in SEQ ID NO: 8.

A second region was selected for expression that contained the final 200 amino acids of the C-terminal region of *L. interrogans* BigL3. This region corresponded to amino acid positions 1687-1886 of SEQ ID NO: 6 in *L. kirschneri* BigL3. The oligonucleotides used to clone this region are:

```
BIGLCTERM1
                                    (SEQ ID NO: 29)
5' aac-ctc-gag-cat-aac-tct-cct-cat-aac 3'

BIGLCTERM2
                                    (SEQ ID NO: 30)
5' ttc-gaa-ttc-tta-ttg-att-ctg-ttg-tct-g 3'
```

PCR amplification with oligonucleotides BIGLCTERM1 and BIGLCTERM2 and purified *L. interrogans* genomic DNA was performed to obtain DNA fragments. These fragments were digested with XhoI and EcoRI enzymes (New Biolabs) and then were ligated into the pRSETA expression vector (Invitrogen) (16). The cloned product was sequenced using vector specific primers and primer walking and the nucleotide sequence of the 600 bp product is shown in SEQ ID NO: 9. The predicted sequence of the encoded 200 amino acid polypeptide, designated BigL3 region 2, is shown in SEQ ID NO: 10.

Figure 7A:
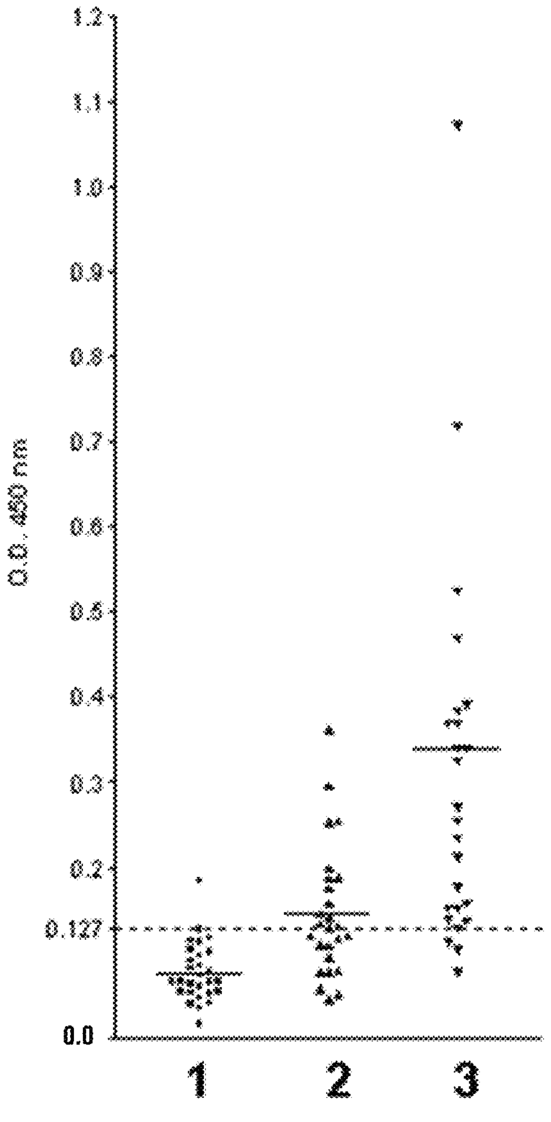
FIGS. 7A-7B shows the rBigL3 IgM (FIG. 7A) and IgG (FIG. 7B) reactivity of sera from 29 individual patients with leptospirosis during the acute (lanes 2) and convalescent (lanes 3) phase of illness and 28 healthy individuals (lanes 1). Sera (1:50 dilutions) and Mu and gamma chain specific antibodies conjugated to horseradish peroxidase were used to determine reactivity. Solid bars represent mean absorbance (OD 450 nm) values.
Figure 7B:
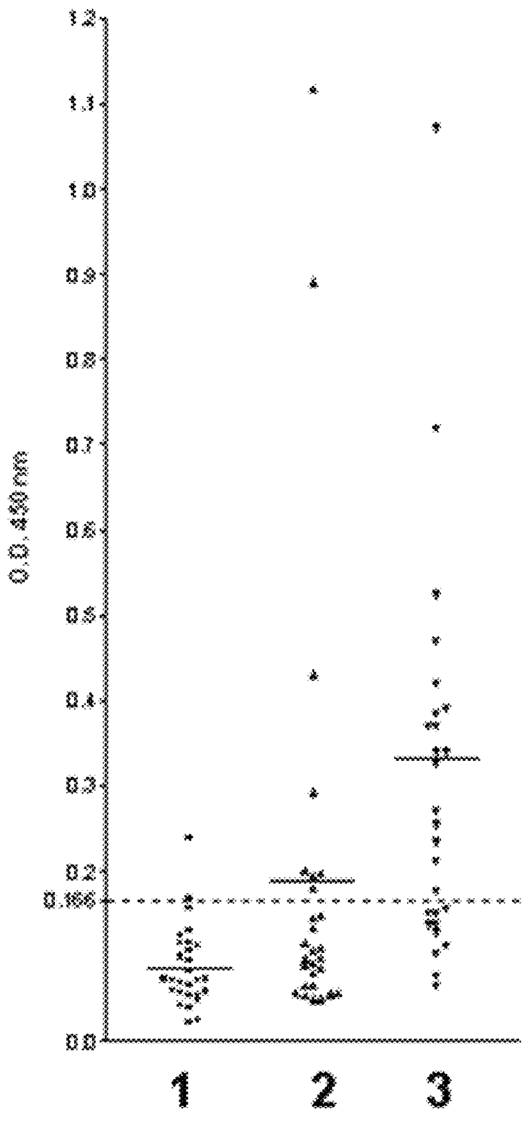

Recombinant proteins, rBigL regions 1 and 2, were expressed in BL21(DE3) pLysogen (Invitrogen). Isopropyl-β-D-thiogalactopyranoside (IPTG; 2 mM final concentration, Life Technologies) was added to log-phase cultures of *E. coli* BLR(DE3)pLysS (Novagen) transformed with pRSET plasmids encoding leptospiral DNA fragments for expression of His6-fusion proteins. 6M guanidine hydrochloride was used to solubilize culture pellets and His6-fusion proteins were purified by affinity chromatography with Ni2+-nitrilotriacetic acid-agarose (Qiagen and Pharmacia). The purity of eluted His6 fusion proteins was assessed by gel electrophoresis and staining with Coomassie brilliant blue. Proteins were dialyzed against PBS, 10% (v/v) glycerol, 0.025% (w/v) sodium azide. After dialysis, the protein concentration was determined with bicinchoninic acid (42). A Ponceau-S (Sigma Chem Co)-stained nitrocellulose membrane after transfer of purified BigL3 region 1 is shown in FIG. 7. The relative mobility of the purified BigL3 was similar to the estimated molecular mass of approximately 58 kD, which was calculated based on the predicted amino acid sequence of the recombinant protein.

EXAMPLE 4

Example 4A

Detection of Antibodies Against Recombinant BigL Proteins

This example illustrates two among several methods that utilize BigL polypeptides to detect antibodies in subject samples. Furthermore, this example provides methods for serodiagnostic kits for identifying infection in subjects suspected of harboring infection.

Immunoblot Detecting of Antibodies to BigL Polypeptides in Samples from Infected Subjects Purified recombinant BigL3 region 2 polypeptide (1 mcg/lane) (Example 3) was subjected to sodium dodecylsulfate-polyacrylamide 12% gel electrophoresis (SDS-PAGE) using a discontinuous buffer system and transferred to nitrocellulose membranes (Osmomics), as previously described (17). The nitrocellulose filter was blocked with TBST with 5% skimmed milk, incubated for more than 1 hour with pooled sera from patients with laboratory confirmed leptospirosis, captured rat (*Rattus norvegicus*) reservoirs of *Leptospira* which had urine and kidney cultures positive for pathogenic *Leptospira*, and experimental laboratory rats and rabbits, immunized with whole *L. interrogans* serovar *copenhageni* strain Fiocruz L1-130 lysates. As control experiments, incubations were performed with sera from healthy individuals from Brazil, captured rats who had no culture or serologic evidence for a *Leptospira* infection and laboratory rats and rabbits prior to immunization. Sera were diluted 1:100 prior to use. After washing, membranes were incubated with goat anti-human gamma chain antibody conjugated to alkaline phosphatase (Sigma), diluted 1:1000, for more than 1 hour. Antigen-antibody complexes were detected by color reaction with NBT (0.3 mg/ml) and BCIP (0.15 mg/ml). Pooled sera from leptospirosis patients, captured rats who were infected with pathogenic leptospires strongly recognized purified recombinant BigL 3 region 1 protein. However, rats immunized with whole *Leptospira* lysates did not visibly bind to the BigL3 polypeptide, indicating that although BigL3 is expressed in cultured leptospires (Example 2, FIG. 4), there may be differential expression of the bigL3 gene. Sufficient quantities of native BigL3 protein may not be present in vitro whereas, during natural infection, leptospires in vivo produce sufficient quantities of BigL3 to induce a strong immune response. Furthermore, this example illustrates that a spectrum of animals produce an immune response to BigL3 during infection and detection of this immune response, and detection of antibodies to recombinant BigL3 polypeptide can be used as a method to identify infection in subjects.

To further illustrate the use of a detection method for antibodies against recombinant BigL3 polypeptide, an immunoblot evaluation was performed with individual sera of patients with laboratory-confirmed leptospirosis, healthy individuals from Brazil and US and patients hospitalized or evaluated in ambulatory clinics with diagnoses other than leptospirosis. The microagglutination test and culture isolation was used to confirm the diagnosis of leptospirosis in patients with clinically-suspected disease (5). The collection of sera from leptospirosis patients was during five-year surveillance for leptospirosis in the city of Salvador, Brazil. The collection of sera from control individuals was obtained from pre-existing serum banks of hospitalized and clinic patients and healthy individuals from Salvador, Brazil and through donations from the Center for Disease Control and Prevention, USA. A list of the sera used is shown in TABLE 1. Sera diluted 1:100 were analyzed following the method described above. The finding of any visible colorization of the 1 mcg band of recombinant BigL3 region 1 polypeptide in the immunoblot was considered a positive reaction.

Figure 8:
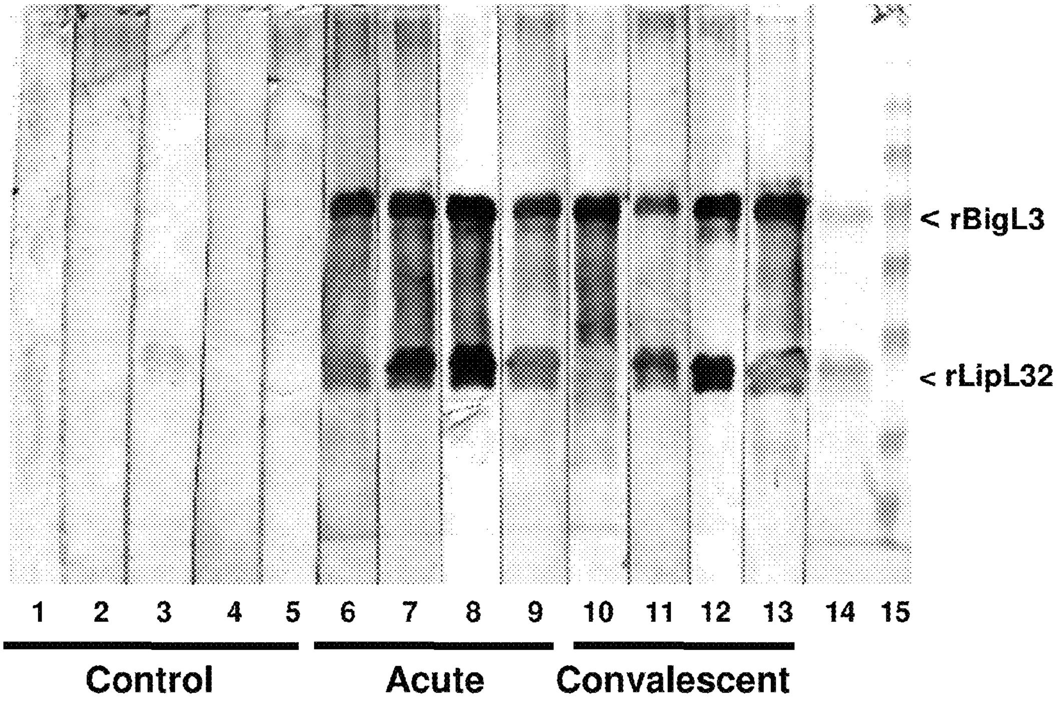
FIG. 8 shows the immunoblot reactivity of individual patients with leptospirosis to rBigL3 during the acute (lanes 6-9) and convalescent (lanes 10-13) phase of illness. Western blot analysis was performed with purified rBigL3 (1 mcg per lane, lanes 3). Membranes were probed with sera diluted 1:100. Gamma chain-specific antibodies conjugated to alkaline phosphatase were used to determine reactivity to the recombinant 58 kD protein of region 1 of BigL3 ($2^{nd}$ to $6^{th}$ Big repeat domains). Reactivity to rLipL32 (1 mcg per lane) was performed as a comparison. The mobility of purified rBigL32 and rLipL32 (lane 14) and molecular mass standards (lane 15) are shown after staining with Ponceau-S and Coomassie blue, respectively.

FIG. 8 illustrates that sera from individual leptospirosis patients react with recombinant BigL3. Table 1 summarizes the findings that demonstrate that more than 90% of hospitalized patients and approximately 70% of outpatients with leptospirosis react to rBigL3 during active infection. All (100%) of the leptospirosis patients react to rBigL3 during the convalescent-phase of their illness. Table 2 compares seroreactivity to rBigL3 with standard diagnostic tests. RBigL3 seroreactivity was greater during the initial phase of illness compared to those observed for standard diagnostic tests. Healthy individuals from the US and 88% of the healthy individuals from Brazil do not react to rBigL3, demonstrating that this reaction to rBigL3 is specific. The specificity of the reaction increases to 100% when it is calculated based on the frequency of IgM seroreactivity among healthy Brazilian individuals. Together, these findings illustrate that the method has utility as a serological marker of active infection and is the basis for a kit that can be used for diagnosis with leptospirosis.

Table 1 also summarizes findings for rBigL3 seroreactivity in endemic regions that have high risk for leptospirosis. 25% of the population that resides in these regions demonstrate rBigL3 IgG seropositivity, indicating that this reaction may be a useful marker to identify past infection. Among patients with confirmed leptospirosis, 56% were seroreactive against rBigL3 during the period two years after their infection with leptospirosis (Table 2). In the period between 2 and 4 years after infection with leptospirosis, 18% demonstrated rBigL3 seroreactivity. Together, these findings illustrate that a kit based on the immunoblot method can detect a past infection with leptospirosis.

Example 4B

ELISA-Based Detection of Antibodies to BigL Polypeptides in Samples from Infected Subjects This example illustrates that ELISA methods are useful in detecting antibodies to BigL polypeptides and in identifying patients with leptospirosis among those with suspected infection. Flat-bottomed polystyrene microtiter plates (Corning) were coated at 4° C. overnight with $His_6$-fusion rBigL3, 0.5-100 ng/well, suspended in 0.05 M sodium carbonate, pH 9.6 (16). The plates were washed twice with distilled water and three times with PBS, 0.05% (v/v) Tween 20 (PBST). Plates were incubated with blocking solution (PBST/1% [w/v] bovine serum albumin) for 2 hours at room temperature and after four washes with PBST, were stored at −20° C. until use. Wells were incubated with 50 μl of sera, diluted 50 to 200-fold in blocking solution, for 1 hour at room temperature with agitation. After four washes with PBST, wells were incubated with 50 μl of 5,000 to 20,000-fold dilutions of anti-human μ or γ-chain goat antibodies conjugated to horseradish peroxidase (Sigma) for 1 hour at room temperature with agitation. Afterwards, plates were washed twice with PBST and three times with PBS and incubated with 50 μl/well of 0.01% (w/v) 3,3',5,5'-tetramethylbenzidine in substrate buffer (0.03% [v/v] hydrogen peroxide, 25 mM citric acid, 50 mM $Na_2HPO_4$, pH 5.0) for 20 minutes in the dark at room temperature. The color reaction was stopped by adding 25 μL 2 N $H_2SO_4$ and the absorbance at 450 nm was measured in an Emax microplate reader (Molecular Devices, Sunnyvale, Calif.).

Initial assays were performed to determine the antigen concentration (mcgs/well) that best discriminated between ELISA reactions of serum samples from laboratory-confirmed leptospirosis cases (n=4) and healthy individuals from an endemic area for leptospirosis in Brazil (n=4). Checkerboard titrations were performed with 50, 100 or 200-fold serum dilutions and antigen concentrations per well of 25, 50, 100 and 200 ng. FIG. 6 illustrates that significantly increased absorbance values were observed at all serum dilutions and rBigL3 polypeptide concentrations for leptospirosis patients than for control individuals.

In subsequent assays to determine sensitivity and specificity, plates were coated with 50 ng of rBigL3. Incubations were performed with 50 and 10,000-fold dilutions of primary sera and secondary antibody conjugate, respectively. Individual serum samples were tested in duplicate and the means of the two measurements were calculated for analysis. Paired measurements that differed by greater than 10% were retested. One positive control serum sample which reacted with all recombinant antigens and one negative control serum sample were included, in duplicate, on each plate as a quality control measure. FIG. 7 illustrates that leptospirosis patients in the acute phase of illness had significantly increased absorbances than control individuals for IgM and IgG seroreactivity (FIG. 7). These differences increased when comparing absorbance values for patients in their convalescent-phase of illness. These experiments illustrate that an ELISA-based method for detecting antibodies against rBigL3 polypeptide is useful for identifying infection with leptospirosis and can be used as a kit for diagnosis.

EXAMPLE 5

Induction of an Immune Response Against *Leptospira* in Subjects

Figure 9:
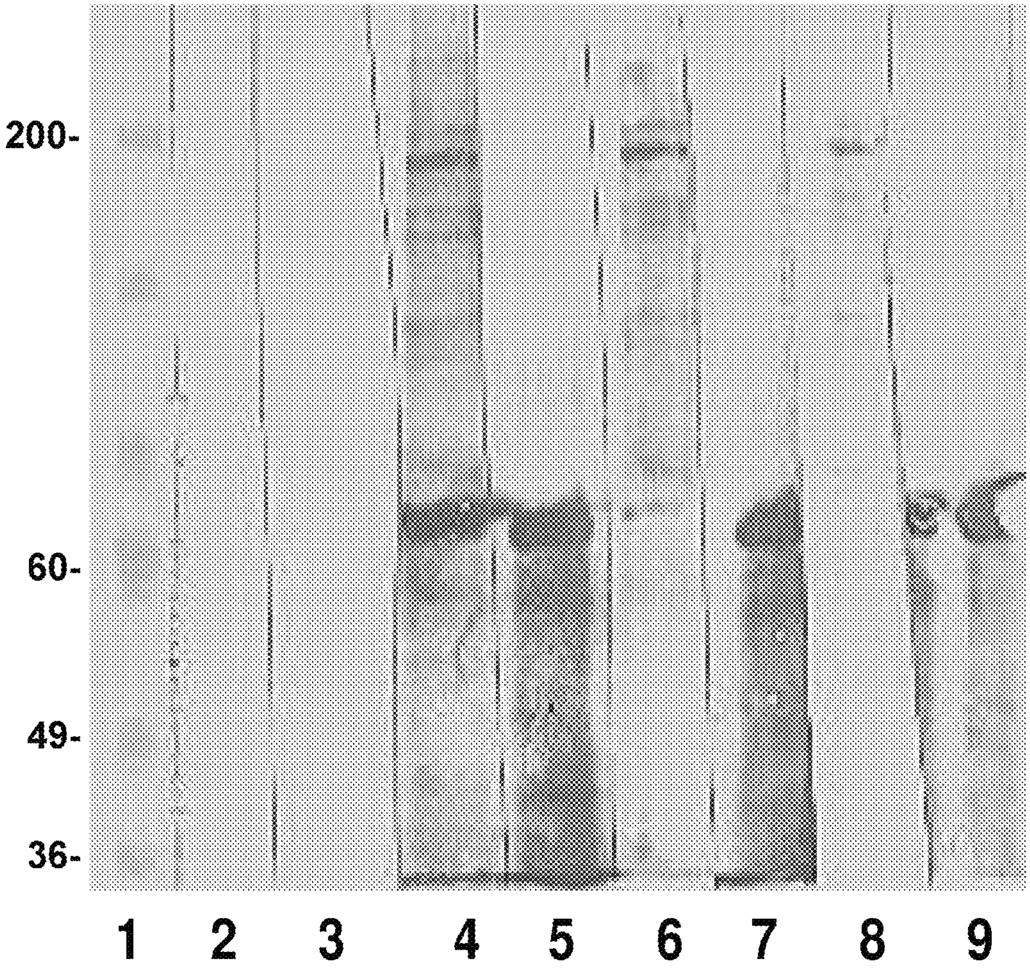
FIG. 9 shows the immunoblot reactivity of rat anti-rBigL3 antisera to rBigL3 and native antigen from *L. interrogans* lysates. Immunoblots were prepared with purified rBigL3 (1 mg/lane; lanes 3, 5, 7, 9) and whole antigen preparations ($10^8$

This example illustrates that an immune response against BigL proteins can be induced via immunization with recombinant BigL proteins. Purified recombinant BigL3 polypeptide derived from *L. interrogans* was obtained with the method described in Example 3. Laboratory rats (Wistar strain) were immunized with 40 mcgs of rBigL3 in Freund's adjuvant (Sigma), and inoculated subcutaneously. Additional immunizations were performed with 20 mcgs of rBigL3 at weeks 3 and 6. Blood was collected 7 weeks after primary immunization and processed for serum. Immunoblots with rBigL3 (1 mcg/lane) were prepared as in Example 4. FIG. 9 illustrates the seroreactivity of rBigL3-immunized rats. rBigL3 was an effective immunogen inducing immunoblot rBigL3 seroreactivity with titers of greater than 1:2500 after a total of three immunizations. Furthermore, antibodies raised to rBigL3 polypeptide recognized native antigens in whole *Leptospira* lysates ($10^8$ leptospires per lane) (FIG. 9). A band with relative mobility at 200 kD is faintly stained in immunoblots as are more intensely staining bands with lower relative mobility, which may represent degradation of the 200 kD or high molecular weight BigL proteins. Seroreactivity against these native antigens is specific since no reactions are observed in the pre-immune sera.

Immunogenicity experiments were performed with purified recombinant BigL polypeptides derived from *L. kirschneri*. Purified recombinant proteins were loaded onto a preparative 12% SDS-PAGE gel and allowed to migrate into the separating gel by electrophoresis. A band containing 100-200 smcg of recombinant protein was excised from the gel, desiccated, ground to powder, dissolved in 1 ml of water, mixed with 1 ml complete Freund's adjuvant (Sigma), and inoculated subcutaneously and intramuscularly in New Zealand white rabbits (Harlan Sprague Dawley) that were free of leptospiral antibodies. Additional immunizations with similar amounts of fusion protein in powdered acrylamide gel mixed with incomplete Freund's adjuvant (Sigma) were administered at four and eight weeks after primary immunization. Blood was collected from the rabbits ten weeks after primary immunization and processed for serum (Harlow, 1988). Immunoblots were performed as previously described (Guerreiro et al. *Infect Immun* 2001) with concentrations of 108 leptospires per lane.

FIG. 10. illustrates that immunization with rBigL3 derived from *L. kirschneri* induces high level antibody titers to native BigL3 polypeptides in *L. kirschneri* and other pathogenic *Leptospira* species such as *L. interrogans*. Together these findings illustrate that immunization with rBigL polypeptides induces an immune response against species of pathogenic spirochetes other than the species used to design the recombinant rBigL polypeptide. Furthermore, the antibodies produced by this method of immunization can be used to detect pathogenic spirochetes in samples.

Finally, this example demonstrates that the presence of native BigL polypeptides is observed in virulent low culture passaged strains and not in avirulent attenuated high culture passaged strains (FIG. 10). Sera from rBigL3-immunized rabbits recognized a predicted 200 kDa corresponding to BigL3 in whole *Leptospira* lysates of virulent and not avirulent attenuated strains. This example illustrates that BigL proteins are markers for virulence and that antibodies against BigL proteins can be used as a method to identify virulent strains. Since BigL may be itself a virulence factor, induction of an immune response to BigL proteins as demonstrated in the example will be useful for application as a vaccine.

TABLE 1

Detection of IgG and IgM antibodies against rBigL and rLipL32 in sera from leptospirosis patients and control groups as determined by the Western Blot method.

| | | rBigL3 seroreactivity | | | rLipL32 seroreactivity | | |
|---|---|---|---|---|---|---|---|
| Study group | No. tested | IgM | IgG | IgM or IgG | IgM | IgG | IgM or IgG |
| | | No. positive reactions (%) | | | | | |
| Hospitalized cases of confirmed leptospirosis | | | | | | | |
| Acute-phase | 52 | 37 (71) | 46 (88) | 48 (92) | 22 (42) | 21 (50) | 38 (73) |
| Convalescent-phase | 52 | 19 (37) | 52 (100) | 52 (100) | 21 (40) | 45 (86) | 46 (88) |
| Outpatient cases of confirmed leptospirosis | | | | | | | |
| Acute-phase | 14 | 6 (42) | 8 (57) | 9 (64) | 2 (14) | 2 (14) | 3 (21) |
| Convalescent-phase | 14 | 7 (50) | 14 (100) | 14 (100) | 6 (42) | 5 (36) | 8 (57) |
| Healthy individual control groups | | | | | | | |
| Non-endemic area (USA) | 30 | 0 (0) | 0 (0) | 0 (0) | 0 (0) | 0 (0) | 0 (0) |
| Endemic area (Brazil) | 40 | 0 (0) | 5 (12) | 5 (12) | 2 (6) | 0 (0) | 2 (6) |
| High risk endemic area (Brazil) | 40 | 0 (0) | 10 (25) | 10 (25) | 4 (10) | 5 (12) | 8 (20) |
| Patient control groups | | | | | | | |
| Dengue | 15 | 0 (0) | 0 (0) | 0 (0) | 0 (0) | 0 (0) | 0 (0) |
| Lyme disease | 15 | 0 (0) | 0 (0) | 0 (0) | 0 (0) | 0 (0) | 0 (0) |
| VDRL-positive | 20 | 0 (0) | 1 (5) | 1 (5) | 0 (0) | 1 (5) | 1 (5) |

TABLE 2

Comparison of the rBigL3 and rLipL32-based Western blot with standard diagnostic tests for leptospirosis.

| | | Standard diagnostic evaluation | | | rBigL Western blot seroreactivity | | | rLipL32 Western blot seroreactivity | | |
|---|---|---|---|---|---|---|---|---|---|---|
| Time period after initiation of illness | No. tested | Median maximum reciprocal MAT titer (range) | Reciprocal MAT titer ≥100 | ELISA-IgM | IgM | IgG | IgM or IgG | IgM | IgG | IgM or IgG |
| | | | | | No. positive reactions (%) | | | | | |
| Acute phase (N = 52)[a] | | | | | | | | | | |
| 2-6 days | 21 | 200 (0-1600) | 12 (57) | 11 (52) | 12 (57) | 16 (76) | 17 (81) | 8 (38) | 8 (38) | 12 (57) |
| 7-15 days | 31 | 400 (0-3200) | 17 (55) | 20 (91) | 25 (81) | 30 (97) | 31 (100) | 14 (45) | 23 (74) | 26 (84) |

TABLE 2-continued

Comparison of the rBigL3 and rLipL32-based Western blot with standard diagnostic tests for leptospirosis.

| | | Standard diagnostic evaluation | | | rBigL Western blot seroreactivity | | | rLipL32 Western blot seroreactivity | | |
|---|---|---|---|---|---|---|---|---|---|---|
| Time period after initiation of illness | No. tested | Median maximum reciprocal MAT titer (range) | Reciprocal MAT titer ≥100 | ELISA-IgM | IgM | IgG | IgM or IgG | IgM | IgG | IgM or IgG |
| | | | | | No. positive reactions (%) | | | | | |
| Early convalescent phase (N = 52) | | | | | | | | | | |
| 16-21 days | 21 | 800 (200-12800) | 21 (100) | 15 (100) | 7 (33) | 21 (100) | 21 (100) | 8 (38) | 18 (86) | 19 (90) |
| 21-30 days | 31 | 1600 (0-6400) | 31 (100) | 21 (100) | 12 (39) | 31 (100) | 31 (100) | 13 (42) | 27 (87) | 27 (87) |
| Early convalescent phase (N = 59) | | | | | | | | | | |
| 0-23 months | 25 | 400 (0-800) | 21 (84) | 24 (96) | 0 (0) | 14 (56) | 14 (56) | 2 (8) | 2 (8) | 3 (12) |
| 24-47 months | 17 | 400 (100-1600) | 17 (100) | 7 (41) | 0 (0) | 3 (18) | 3 (18) | 2 (12) | 2 (12) | 3 (18) |
| 48-78 months | 17 | 200 (0-800) | 15 (88) | 5 (29) | 0 (0) | 3 (18) | 3 (18) | 2 (12) | 1 (6) | 3 (18) |

[a]Acute-phase serum samples were collected upon hospital admission.

REFERENCES

1. Levett P N. Leptospirosis. *Clin Microbiol Rev.* 2001; 14(2): 296-326.
2. Faine S B, Adler B, Bolin C, Perolat P. *Leptospira and leptospirosis.* 2nd ed Melbourne, Australia: MediSci; 1999.
3. Farr R W. Leptospirosis. *Clin Infect Dis.* 1995; 21(1):1-6; quiz 7-8.
4. Lomar A V, Diament D, Tones J R. Leptospirosis in Latin America. *Infect Dis Clin North Am.* 2000; 14(1):23-39, vii-viii.
5. Ko A I, Galvao Reis M, Ribeiro Dourado C M, Johnson W D, Jr., Riley L W. Urban epidemic of severe leptospirosis in Brazil. Salvador Leptospirosis Study Group. *Lancet.* 1999; 354(9181):820-5.
6. Bughio N I, Lin M, Surujballi O P. Use of recombinant flagellin protein as a tracer antigen in a fluorescence polarization assay for diagnosis of leptospirosis. *Clin Diagn Lab Immunol.* 1999; 6(4):599-605.
7. Park S H, Ahn B Y, Kim M J. Expression and immunologic characterization of recombinant heat shock protein 58 of *Leptospira* species: a major target antigen of the humoral immune response. *DNA Cell Biol.* 1999; 18(12):903-10.
8. Haake D A, Walker E M, Blanco D R, Bolin C A, Miller M N, Lovett M A. Changes in the surface of *Leptospira interrogans* serovar *grippotyphosa* during in vitro cultivation. *Infect Immun.* 1991; 59(3):1131-40.
9. Haake D A, Champion C I, Martinich C, et al. Molecular cloning and sequence analysis of the gene encoding OmpL1, a transmembrane outer membrane protein of pathogenic *Leptospira* spp. *J Bacterial.* 1993; 175(13): 4225-34.
10. Haake D A, Martinich C, Summers T A, et al. Characterization of leptospiral outer membrane lipoprotein LipL36: downregulation associated with late-log-phase growth and mammalian infection. *Infect Immun.* 1998; 66(4):1579-87.
11. Haake D A, Mazel M K, McCoy A M, et al. Leptospiral outer membrane proteins OmpL1 and LipL41 exhibit synergistic immunoprotection. *Infect Immun.* 1999; 67(12): 6572-82.
12. Haake D A, Chao G, Zuerner R L, et al. The leptospiral major outer membrane protein LipL32 is a lipoprotein expressed during mammalian infection. *Infect Immun.* 2000; 68(4):2276-85.
13. Shang E S, Exner M M, Summers T A, et al. The rare outer membrane protein, OmpL1, of pathogenic *Leptospira* species is a heat-modifiable porin. *Infect Immun.* 1995; 63(8): 3174-81.
14. Shang E S, Summers T A, Haake D A. Molecular cloning and sequence analysis of the gene encoding LipL41, a surface-exposed lipoprotein of pathogenic *Leptospira* species. *Infect Immun.* 1996; 64(6):2322-30.
15. Yelton D B, Charon N W. Cloning of a gene required for tryptophan biosynthesis from *Leptospira biflexa* serovar patoc into *Escherichia coli. Gene.* 1984; 28(2):147-52.
16. Flannery B, Costa D, Carvalho F P, et al. Evaluation of recombinant *Leptospira* antigen-based enzyme-linked immunosorbent assays for the serodiagnosis of leptospirosis. *Journal of Clinical Microbiology.* 2001; 39(9):3303-3310.
17. Guerreiro H, Croda J, Flannery B, et al. Leptospiral proteins recognized during the humoral immune response to leptospirosis in humans. *Infect Immun.* 2001; 69(8):4958-68.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A recombinant expression vector comprising a heterologous polynucleotide molecule encoding a polypeptide comprising an amino acid sequence greater than 90% identical to the amino acid sequence set forth as SEQ ID NO: 8.

2. The vector of claim 1, wherein the heterologous polynucleotide is linked to a promoter.

3. The vector of claim 1, wherein the polynucleotide molecule is from a *Leptospira* species.

4. The vector of claim 1, wherein the encoded polypeptide comprises the amino acid sequence set forth as SEQ ID NO: 8.

5. The vector of claim 4, wherein the encoded polypeptide consists of the amino acid sequence set forth as SEQ ID NO: 8.

6. The vector of claim 1, wherein the polynucleotide comprises a nucleic acid sequence greater than 90% identical to the nucleic acid sequence set forth as SEQ ID NO: 7.

7. The vector of claim 6, wherein the polynucleotide comprises the nucleic acid sequence set forth as SEQ ID NO: 7.

8. The vector of claim 7, wherein the polynucleotide consists of the nucleic acid sequence set forth as SEQ ID NO: 7.

9. A host cell comprising the vector of claim 1.

10. A method of producing a recombinant polypeptide, comprising purifying the recombinant polypeptide from the host cell of claim 9.

11. A method of producing a recombinant polypeptide, comprising:

transforming a cell with the recombinant vector of claim 2;

expressing the polypeptide from the vector in the transformed cell; and purifying the recombinant polypeptide.

* * * * *